(12) United States Patent
Bian et al.

(10) Patent No.: US 10,254,247 B2
(45) Date of Patent: Apr. 9, 2019

(54) ION MOBILITY SPECTROMETER CLEAR-DOWN

(75) Inventors: Qunzhou Bian, Mississaugua (CA); John J. Carroll, Morristown, NJ (US)

(73) Assignee: SMITHS DETECTION MONTREAL INC., Laval (CA)

( * ) Notice: Subject to any disclaimer, the term of this patent is extended or adjusted under 35 U.S.C. 154(b) by 1278 days.

(21) Appl. No.: 13/881,817

(22) PCT Filed: Oct. 27, 2011

(86) PCT No.: PCT/US2011/058046
§ 371 (c)(1),
(2), (4) Date: Jul. 5, 2013

(87) PCT Pub. No.: WO2012/058406
PCT Pub. Date: May 3, 2012

(65) Prior Publication Data
US 2013/0298938 A1    Nov. 14, 2013

Related U.S. Application Data

(60) Provisional application No. 61/407,342, filed on Oct. 27, 2010, provisional application No. 61/407,335, (Continued)

(51) Int. Cl.
*B08B 6/00* (2006.01)
*H01J 49/04* (2006.01)
(Continued)

(52) U.S. Cl.
CPC ............ *G01N 27/622* (2013.01); *B08B 6/00* (2013.01); *G01N 23/00* (2013.01); *G06K 9/0053* (2013.01);
(Continued)

(58) Field of Classification Search
CPC .... G01N 27/622; G01N 23/00; G06K 9/0053; H01J 49/025; H01J 49/04; H01J 49/06
See application file for complete search history.

(56) References Cited

U.S. PATENT DOCUMENTS 5,554,846 A * 9/1996 Regiec ................. G01N 1/2273
250/287
7,417,222 B1    8/2008 Pfeifer et al.
(Continued)

FOREIGN PATENT DOCUMENTS

EP          2633297       2/2015
WO       2012056322       5/2012
(Continued)

OTHER PUBLICATIONS

European Search Report, EP Patent Application No. 14193536.1, dated May 13, 2015.
(Continued)

*Primary Examiner* — Douglas Lee
(74) *Attorney, Agent, or Firm* — Casimir Jones SC; David W. Staple

(57) ABSTRACT

Method and systems for managing clear-down are provided. The method can include generating a clear-down trigger associated with an ion mobility spectrometer and operating the ion mobility spectrometer in fast clear-down mode in response to the clear-down trigger. Methods and systems can further provide that where the ion mobility spectrometer operates in fast-switching mode, the ion mobility spectrometer alternating a plurality of times between operation according to a positive ion mode and operation according to a negative ion mode, and further operating according to the positive ion mode for less than about 1 second before switching to the operation according to the negative ion mode, and operating according to the negative ion mode for less than about 1 second before switching to the operation according to the positive ion mode.

20 Claims, 17 Drawing Sheets

Related U.S. Application Data filed on Oct. 27, 2010, provisional application No. 61/407,327, filed on Oct. 27, 2010.

(51) Int. Cl.
*H01J 49/06* (2006.01)
*G01N 27/62* (2006.01)
*H01J 49/00* (2006.01)
*G06K 9/00* (2006.01)
*H01J 49/02* (2006.01)
*G01N 23/00* (2006.01)

(52) U.S. Cl.
CPC ........ *H01J 49/0031* (2013.01); *H01J 49/025* (2013.01); *H01J 49/04* (2013.01); *H01J 49/06* (2013.01); *H01J 49/061* (2013.01)

(56) References Cited

U.S. PATENT DOCUMENTS

| | | | |
|---|---|---|---|
| 2002/0134933 A1* | 9/2002 | Jenkins | G01N 27/622 250/287 |
| 2004/0119591 A1* | 6/2004 | Peeters | G08B 21/0222 340/539.26 |
| 2009/0322338 A1* | 12/2009 | Godefroy | G01V 3/24 324/355 |
| 2010/0180913 A1* | 7/2010 | Arena | C23C 16/4405 134/2 |
| 2011/0220790 A1* | 9/2011 | Sun | G01N 15/0266 250/288 |
| 2013/0284914 A1 | 10/2013 | Zaleski et al. | |
| 2013/0297227 A1 | 11/2013 | Burton et al. | |

FOREIGN PATENT DOCUMENTS

| | | |
|---|---|---|
| WO | 2012058406 | 5/2012 |
| WO | 2012058407 | 5/2012 |

OTHER PUBLICATIONS

Anonymous, Quantum Sniffer QS-H150 Explosives Detector, Implant Sciences Corporation Product Information, 2008, 2 pages.
International Search Report and Written Opinion for PCT/US2011/058046, dated Mar. 8, 2012, 11 pages.

* cited by examiner

SWITCH CLOSED

SWITCH OPEN

ION MOBILITY SPECTROMETER CLEAR-DOWN

CROSS-REFERENCE TO RELATED APPLICATIONS

This application claims the benefit of U.S. Provisional Patent Application Ser. No. 61/407,335, filed Oct. 27, 2010, U.S. Provisional Patent Application Ser. No. 61/407,327, filed Oct. 27, 2010, and U.S. Provisional Patent Application Ser. No. 61/407,342, filed Oct. 27, 2010, each of which is incorporated by reference in its entirety.

FIELD OF THE INVENTION

This application is directed to the maintenance of ion mobility spectrometers.

BACKGROUND OF THE INVENTION

Ion mobility spectrometry is a method used to identify the composition of a sample of ions using ion mobility. Ion mobility spectrometers can be employed at security checkpoints, such as airports, to assist in the detection of explosives and narcotics. When used at airports, for example, residue from luggage can be transferred to a swab, which can be manipulated so that molecules and/or atoms associated with the residue pass into an ionization region within the ion mobility spectrometer. In the ionization region, the molecules and atoms associated with the residue can be ionized. Both positive and negative ions can form in the ionization region. An electric field at grids spaced between the ionization region and a drift region can be pulsed to allow ions to pass from the ionization region into the drift region. The ions in the drift region can be further subject to a force as a result of an electric field maintained in the drift region. Once in the drift region, the ions can separate based upon the ions' respective ion mobility. In this way, a time-of-flight measurement of the ions in the drift region (which can be measured as a change in current magnitude on a collector plate at one end of the drift region), can provide an identifying peak in a measured current magnitude, and which can be associated with a particular ion. The plot of current magnitude at the collector as a function of time is referred to as a plasmagram.

SUMMARY

In one aspect, embodiments provide a method of managing clear-down. The method can include operating the ion mobility spectrometer in fast-switching mode in response to a clear-down trigger. Embodiments can further provide that the ion mobility spectrometer in fast-switching mode alternates a plurality of times between operation according to a positive ion mode and operation according to a negative ion mode, and further operates in positive ion mode for less than about 1 second before switching to negative ion mode, and operates in negative ion mode for less than about 1 second before switching to positive ion mode.

In another aspect, embodiments can provide an ion mobility spectrometer that can include a repelling grid, a gating grid, an ionization region, a drift region, and a collector. Embodiments can further provide that the ionization region, the repelling grid, the gating grid, and the drift region are configured to switch from positive ion mode to negative ion mode in fast-switching mode. Further still, embodiments can provide that the ionization region, the repelling grid, the gating grid, and the drift region are configured to switch from negative ion mode to positive ion mode in fast-switching mode, and wherein the ion mobility spectrometer is configured to be responsive to a clear-down trigger so the ion mobility spectrometer operates in fast-switching mode. In this aspect, an ion mobility spectrometer in fast-switching mode can operate in positive ion mode for less than about 1 second before switching to negative ion mode, and can operate in negative ion mode for less than about 1 second before switching to positive ion mode.

In a further aspect, embodiments can provide a computer-readable medium comprising instructions stored thereon, wherein the instructions cause a processor to perform a method of managing fast clear-down. The method can include operating an ion mobility spectrometer in fast-switching mode in response to a clear-down trigger. Embodiments consistent with the present disclosure can further provide that the ion mobility spectrometer in fast-switching mode alternates a plurality of times between operation in positive ion mode and operation in negative ion mode, and further operate in positive ion mode for less than about 1 second before switching to the negative ion mode, and operate in negative ion mode for less than about 1 second before switching to positive ion mode.

Additional features and embodiments of the invention will be set forth in part in the description which follows, and in part will be obvious from the description, or may be learned by practice of the invention. It is to be understood that both the foregoing general description and the following detailed description are exemplary and explanatory only and are not restrictive of the claimed subject matter.

BRIEF DESCRIPTION OF THE DRAWINGS

The accompanying drawings, which are incorporated in and constitute a part of this specification, illustrate exemplary embodiments and together with the description, serve to explain the principles of the disclosure.

DETAILED DESCRIPTION

Reference will now be made in detail to the disclosed embodiments of the disclosure, examples of which are illustrated in the accompanying drawings. Wherever possible, the same reference numbers will be used throughout the drawings to refer to the same or like parts.

Figure 1:
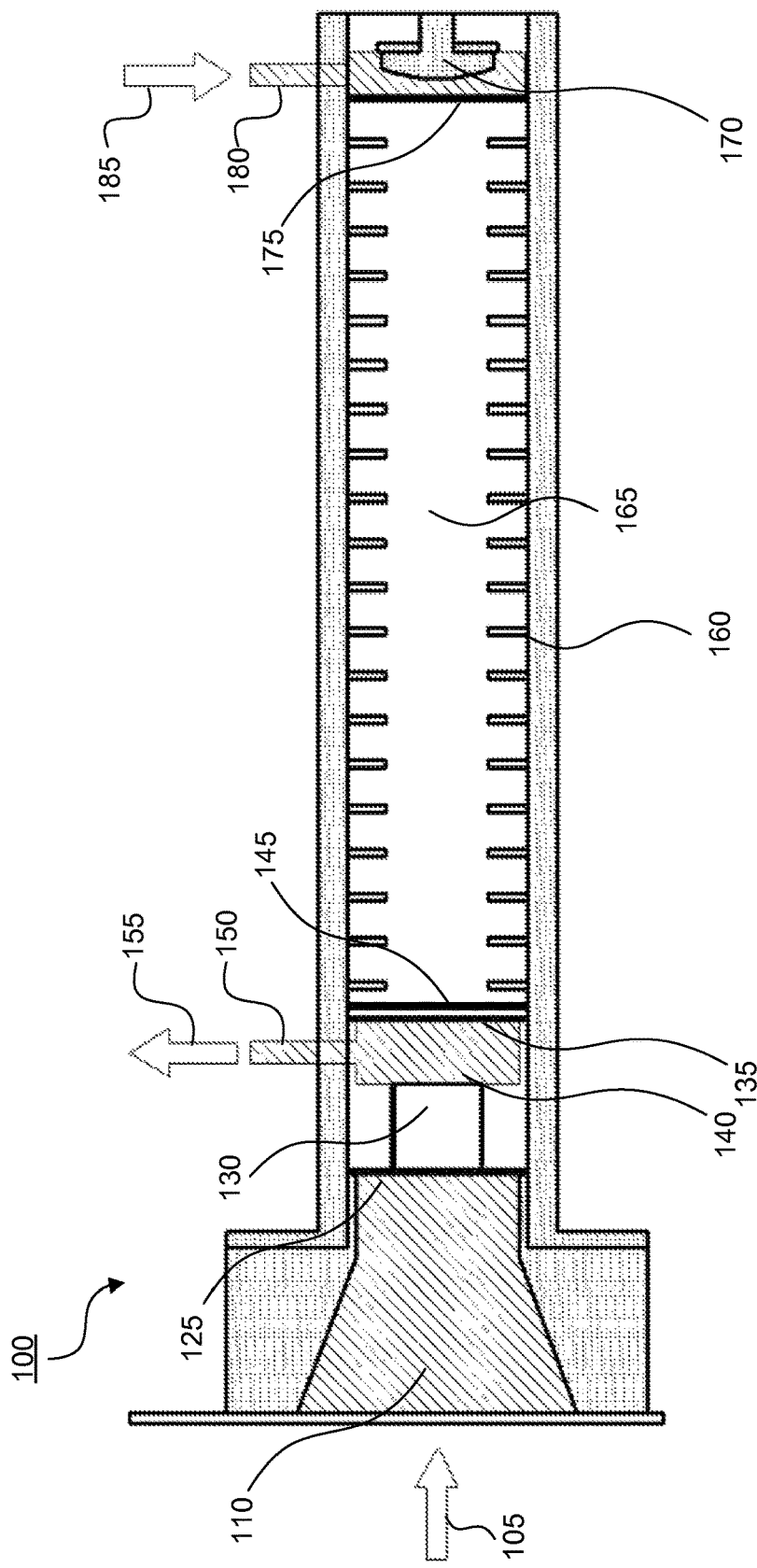
FIG. 1 is a cross-sectional view of an ionization region and a drift region of an ion mobility spectrometer consistent with an embodiment.

A portion of an ion mobility spectrometer 100 consistent with an embodiment of the current disclosure is depicted in FIG. 1. Molecules and/or atoms associated with a sample being tested can enter through an inlet 110 (depicted with arrow 105). Sample molecules and/or atoms then pass a repelling grid 125 into an ionization region 140. The repelling grid 125 can comprise inert metal (e.g., gold-plated nickel), and can have a grid spacing of about 0.1 mm. The ionization region 140 can include a region with an ionization source 130. The ionization source 130 can comprise a material such as Nickel-63. Alternatively, ions can be created in ionization region 140 as a result of corona discharge ionization, photoionization, electrospray ionization, matrix assisted laser desorption ionization (MALDI), or the like.

The ion mobility spectrometer 100 can operate in positive ion mode and negative ion mode. In these modes, certain components of the ion mobility spectrometer 100 can exhibit voltages in order to create an electric field along the length of the ion mobility spectrometer 100. When the ion mobility spectrometer 100 is operating in positive ion mode, for example, the repelling grid 125 can exhibit a relatively high positive voltage. As described further below, when operating in positive ion mode, other components of ion mobility spectrometer 100 located towards the opposite end of the ionization region 140 and across the drift region 160 will exhibit lower voltages. This configuration will create an electric field in the ionization region 140, for example, that directs positive ions away from the inlet 110. In an embodiment, the magnitude of the positive voltage on the repelling grid 125 can be about 2100 V. The range of magnitudes of the positive voltage on the repelling grid 125 can be 1000V to 5000V. Example values can be higher or lower depending upon the physical dimensions of the system. Both a fixed grid 135 and a gating grid 145 are located between the ionization region 140 and the drift region 165. As discussed above, and in positive ion mode, the fixed grid 135 can exhibit a voltage that is less than the positive voltage on the repelling grid 125 such that there is a potential gradient (i.e., an electric field) oriented across the ionization region 140. Other components can also be present between the repelling grid 125 and the fixed grid 135 in the ionization region 140 in support of an electric field in the ionization region 140. In an embodiment, when the voltage on the repelling grid 125 is approximately 2100 V as described above, the fixed grid 135 can exhibit a positive voltage that is approximately 1810 V. The voltage on the fixed grid 135 can be chosen so the potential gradient near the fixed grid 135 in the ionization region 140 and near the fixed grid 135 in the drift region 165 will provide a force on ions that will direct the ions from the ionization region 140 to the drift region 165 when the gating grid 145 is "open" (as is described further below). By way of example only, and without limitation, a configuration that allows for a uniform electric field across the barrier between the ionization region 140 and the drift region 165 is a configuration that can provide a uniform force on an ion to direct ions (of one polarity) from the ionization region 140 to the drift region 165. According to the above embodiment, an electric field across the ionization region 140 can have a magnitude that ranges from 50 V/cm to 500 V/cm. The electric field in the ionization region 140 does not need to be uniform throughout the ionization region 140. However, the electric field in the drift region 165 can be generally uniform. For example, where the drift region 165 is approximately 6.9 cm, and the electric field across the drift region 165 also has a magnitude of 250 V/cm, the voltage on a guard grid 175 at one end of drift region 165 can be approximately 90 V. In other embodiments, the range of values for an electric field in the drift region 165 can be 200 V/cm to 300 V/cm.

Adjacent to the fixed grid 135 is the gating grid 145, where the gating grid 145 can be positioned so the fixed grid 135 is between the repelling grid 125 and the gating grid 145. The gating grid 145 can be approximately 0.75 mm from the fixed grid 135. A shutter structure consistent with the combination of the fixed grid 135 and the gating grid 145 is referred to as a Bradbury-Nielsen gate. (Without limitation, another shutter structure consistent with the present disclosure is a Tyndall's gate.) The combination of the fixed grid 135 and the gating grid 145 can comprise two sets of parallel wires (which can be two etched foils), where the spacing between the wires of the respective grids can be about 0.8 mm. The parallel wires on the grids can be oriented in the same direction, but can be spaced so that, when viewed from a direction that is perpendicular to the plane of the grids, the wires are interleaved. There can also be an insulating foil of thickness about 0.75 mm between the grids. The fixed grid 135 and the gating grid 145 can comprise Invar or other materials. In positive ion mode, the gating grid 145 can be kept at a higher voltage than the fixed grid 135 to create a barrier along the potential gradient between the ionization region 140 and the drift region 165. When the gating grid 145 is at a higher potential than the fixed grid 135, the gating grid 145 is referred to as "closed." The difference in voltage between the gating grid 145 and the fixed grid 135, when the gating grid 145 is closed, can be about 20 V. The voltage of the gating grid 145 can have a magnitude of about 1830 V in positive ion mode. Such a magnitude can have the effect of introducing an electric field that interferes with the passage of positive ions from the ionization region 140 through the drift region 165 to a collector 170 (described further below).

After molecules and/or atoms have entered the ionization region 140 and positive ions form, the repelling grid 125 can be maintained at a high voltage as described above and the gating grid 145 can remain closed for approximately 20 milliseconds. After this time period elapses, a negative voltage pulse can be applied to the gating grid 145 to open the gating grid 145 and allow positive ions to move from the ionization region 140 to the drift region 165 so the positive ions may travel toward the collector 170. In an embodiment, when the gating grid 145 is approximately 20 V higher than the fixed grid 135 when closed, the negative voltage pulse to the gating grid 145 can have an amplitude of approximately 25 V to open the gating grid 145. In an embodiment, the negative voltage pulse applied to the gating grid 145 to open the gating grid 145 can have an amplitude so the potential gradient at the boundary between the ionization region 140 and the drift region 165 directs positive ions from the ionization region 140 to the drift region 165 so positive ions can arrive at the collector 170. A time period permitted for the ions to move from the ionization region 140 to the drift region 165 (when the gating grid 145 is open) can be about 200 microseconds. The gating grid 145 can be open for about 200-300 microseconds, but can be open for as short as about 50 microseconds and open for as long as about 1000 microseconds. Opening the shutter structure (such as by pulsing the voltage on the gating grid 145) for this duration, and then closing the shutter structure can allow positive ions to move into the drift region 165 so the positive ions can arrive at the collector 170. In the drift region 165, an electric field can provide a force on the positive ions to direct the positive ions through the drift region 165 towards the guard grid 175 and the collector 170. The collector 170 can be any suitable structure for detecting pulses of current associated with moving ions, such as a Faraday plate. As the positive ions move through the drift region 165 towards the collector 170, the positive ions can move through a drift gas. In an embodiment, the drift gas can move in the opposite direction to the flow of the positive ions, where the flow of positive ions is towards the collector 170. The drift gas can enter the drift region 165 from a drift flow 180 (indicated by arrow 185) and exit the ion mobility spectrometer 100 through an exhaust flow 150 (indicated by arrow 155). The drift gas in the drift region 165 can be dry air, although other gases such as nitrogen or helium can be used. As the ions move through the drift region 165 toward the collector 170, the various species of ions can separate as a function of their mobility. The drift time of the ions across the drift region 165 can vary, depending on their atomic and molecular characteristics and the temperature and pressure of the drift gas. For a drift region that is approximately 6.9 cm in length and at normal atmospheric pressure and temperature, the drift time can be in the range of 5 milliseconds to 20 milliseconds. Furthermore, the time period during which data is acquired from the collector 170 associated with one scan can range from about 2 milliseconds to about 40 milliseconds. In an embodiment, one scan can represent a 25 millisecond time period.

Accordingly, electric current values can be measured at regular time intervals at the collector 170, corresponding to time-of-flight signatures of the ionic species that can make up the positive ions present in the drift region 165. As discussed above, in an embodiment, the drift gas can flow in the opposite direction from the movement of the positive ions being measured at the collector 170 in positive ion mode. Such a drift gas flow can be used to keep the drift gas pure, but a flow is not required for operation of the ion mobility spectrometer 100. Other methods and systems for maintaining drift gas purity can include placing sorbent material within the drift region 165.

In an embodiment, as described above, the voltage difference between the gating grid 145 and the guard grid 175 can be approximately 1720 V and the distance between the gating grid 145 and the guard grid 175 can be 6.9 cm. The magnitude of the voltage of the guard grid 175 can be approximately 90 V.

Drift rings 160 can be employed in drift region 165. In an embodiment, the drift rings 160 can be flat metal rings, spaced at regular intervals between the gating grid 145 and the guard grid 175 and can be biased at equal voltage steps to improve uniformity of the potential gradient (that is, the uniformity of the electric field) within the drift region 165.

Operation of the ion mobility spectrometer 100 in negative ion mode is similar, in principle, to its operation in positive ion mode. The relative voltages on the repelling grid 125, the fixed grid 135, the gating grid 145, and the guard grid 175, however, are inverted. Specifically, the repelling grid 125 can be more negative than the fixed grid 135, which can be more negative than the guard grid 175. In an embodiment of the ion mobility spectrometer 100 operating in negative ion mode, the magnitude of the voltages associated with the repelling grid 125, the fixed grid 135, the gating grid 145, and the guard grid 175 can be approximately similar in magnitude but with opposite polarity to those recited above in positive mode. Specifically, the repelling grid 125 can be approximately −2100 V, the fixed grid 135 can be approximately −1810 V, the guard grid 175 can be approximately −90 V, and the gating grid 145 can be approximately −1830 V when closed, and pulsed to approximately −1805 V when open. The voltage across the drift rings 160 can also be inverted from the circumstance described in positive ion mode to form a uniform potential gradient through the drift region 165. In this way, the potential gradient in negative ion mode is inverted from the potential gradient described above in connection with positive ion mode, thereby inverting the direction of the electric field across the ionization region 140 and the drift region 165 of the ion mobility spectrometer 100.

As described above, the drift region 165 can have an electric field applied along its length, and the slope of the potential field as a function of distance (i.e., the direction of the electric field associated with the potential gradient) can be positive or negative depending on the charge of the ions. Ions of a similar polarity can move from the ionization region 140 into the drift region 165 by the opening and closing of the gating grid 145. The time period of a scan of a collection of ions in the drift region 165 is the time period between when the gating grid 145 opens to admit ions into the drift region 165 from the ionization region 140, and the subsequent opening of the gating grid 145 to admit additional ions into the drift region 165 from the ionization region 140. The interval between subsequent voltage pulses applied to gating grid 145 so that it opens (i.e., negative voltage pulses for operation in positive ion mode and positive voltage pulses for operation in negative ion mode) is referred to as the "scan period." Current measurements that are acquired from the collector 170 from several subsequent scans can be co-added together to improve signal-to-noise of the mobility spectrum reflected in the scans. This collection of data is referred to as a "segment." Data associated with one segment can be acquired in less than a second (i.e., data associated with one segment can be acquired by co-adding approximately 40 scans or less, where the scans have a duration of approximately 25 milliseconds). A series of sequential segments, with characteristic ion peak patterns, can be obtained and can be displayed either as a series of individual segments versus desorption time in seconds (a three-dimensional plasmagram) or as an average of all segments obtained during the analysis (a two-dimensional plasmagram). The desorption time is the time associated with the desorption of molecules and atoms from the swab, such as through the application of heat. The desorption of the molecules and atoms from the swab through the application of heat, for example, can make the molecules and atoms available to pass through the inlet 110 and into the ionization region 140.

As described above, in positive ion mode, the gating grid 145 can be kept at a higher voltage than the fixed grid 135 to create a barrier along the potential gradient between the ionization region 140 and the drift region 165. When the gating grid 145 is at a higher potential than the fixed grid 135, the gating grid 145 is referred to as "closed." Further, as described above, the difference in voltage between the gating grid 145 and the fixed grid 135, when the gating grid 145 is closed, can be about 20 V. Such a magnitude can have the effect of supporting an electric field that interferes with the passage of positive ions from the ionization region 140 through the drift region 165 to the collector 170. Moreover, a negative voltage pulse can be applied to the gating grid 145 to open the gating grid 145 and allow positive ions to move from the ionization region 140 to the drift region 165 so the positive ions may travel toward the collector 370. In an embodiment, when the gating grid 145 is approximately 20 V higher than the fixed grid 135 when closed, the negative voltage pulse to the gating grid 145 can have an amplitude of approximately 25 V to open the gating grid 145. In a further embodiment, a positive voltage pulse of approximately 25 V can be applied to the fixed grid 135, while the gating grid 145 is left unchanged in order to "open" the shutter structure associated with the combination of the fixed grid 335 and the gating grid 345 in positive ion mode. That is, in a further embodiment, and rather than applying a negative voltage pulse to the gating grid 145 while the fixed grid 135 is left unchanged, a positive voltage pulse can be applied to the fixed grid 135 while the gating grid 145 is left unchanged. Further still, in further embodiments, a positive voltage pulse of approximately N volts can be applied to the fixed grid 135 and a negative voltage pulse of approximately 25–N volts can be applied to the gating grid 145 in order to "open" the shutter structure associated with the combination of the fixed grid 135 and the gating grid 145 in positive ion mode.

Further still, and as described above, in negative ion mode, the gating grid 145 can be kept at a lower voltage than the fixed grid 135 to create a barrier along the potential gradient between the ionization region 140 and the drift region 165. When the gating grid 145 is at a lower potential than the fixed grid 135, the gating grid 145 is referred to as "closed." Further, as described above, the difference in voltage between the gating grid 145 and the fixed grid 135, when the gating grid 145 is closed, can be about 20 V. Again, such a magnitude can have the effect of supporting an electric field that interferes with the passage of negative ions from the ionization region 140 through the drift region 165 to the collector 170. Further still, a positive voltage pulse can be applied to the gating grid 145 to open the gating grid 145 and allow negative ions to move from the ionization region 140 to the drift region 165 so the negative ions may travel toward the collector 170. In an embodiment, when the gating grid 145 is approximately 20 V lower than the fixed grid 135 when closed, the positive voltage pulse to the gating grid 145 can have an amplitude of approximately 25 V to open the gating grid 145. In a further embodiment, a negative voltage pulse of approximately 25 V can be applied to the fixed grid 135, while the gating grid 145 is left unchanged in order to "open" the shutter structure associated with the combination of the fixed grid 135 and the gating grid 145 in negative ion mode. That is, in a further embodiment, and rather than applying a positive voltage pulse to the gating grid 145 while the fixed grid 135 is left unchanged, a negative voltage pulse can be applied to the fixed grid 135 while the gating grid 145 is left unchanged. In further embodiments, a negative voltage pulse of approximately N volts can be applied to the fixed grid 135 and a positive voltage pulse of approximately 25–N volts can be applied to the gating grid 145 in order to "open" the shutter structure associated with the combination of the fixed grid 135 and the gating grid 145 in negative ion mode.

Figure 2:
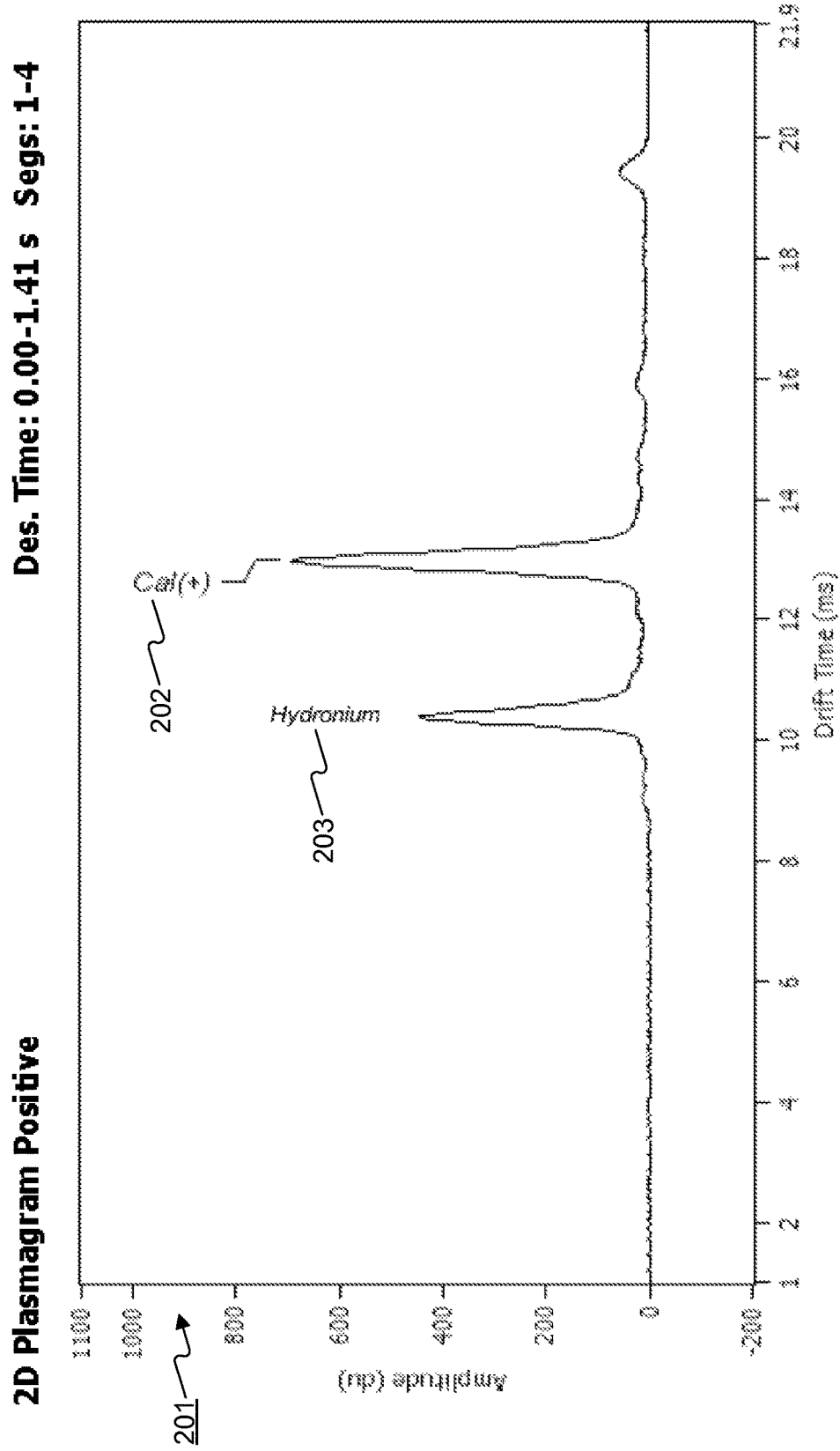
FIG. 2 depicts an example two-dimensional plasmagram associated with a first set of segment measurements of a blank swab in positive ion mode.
Figure 3:
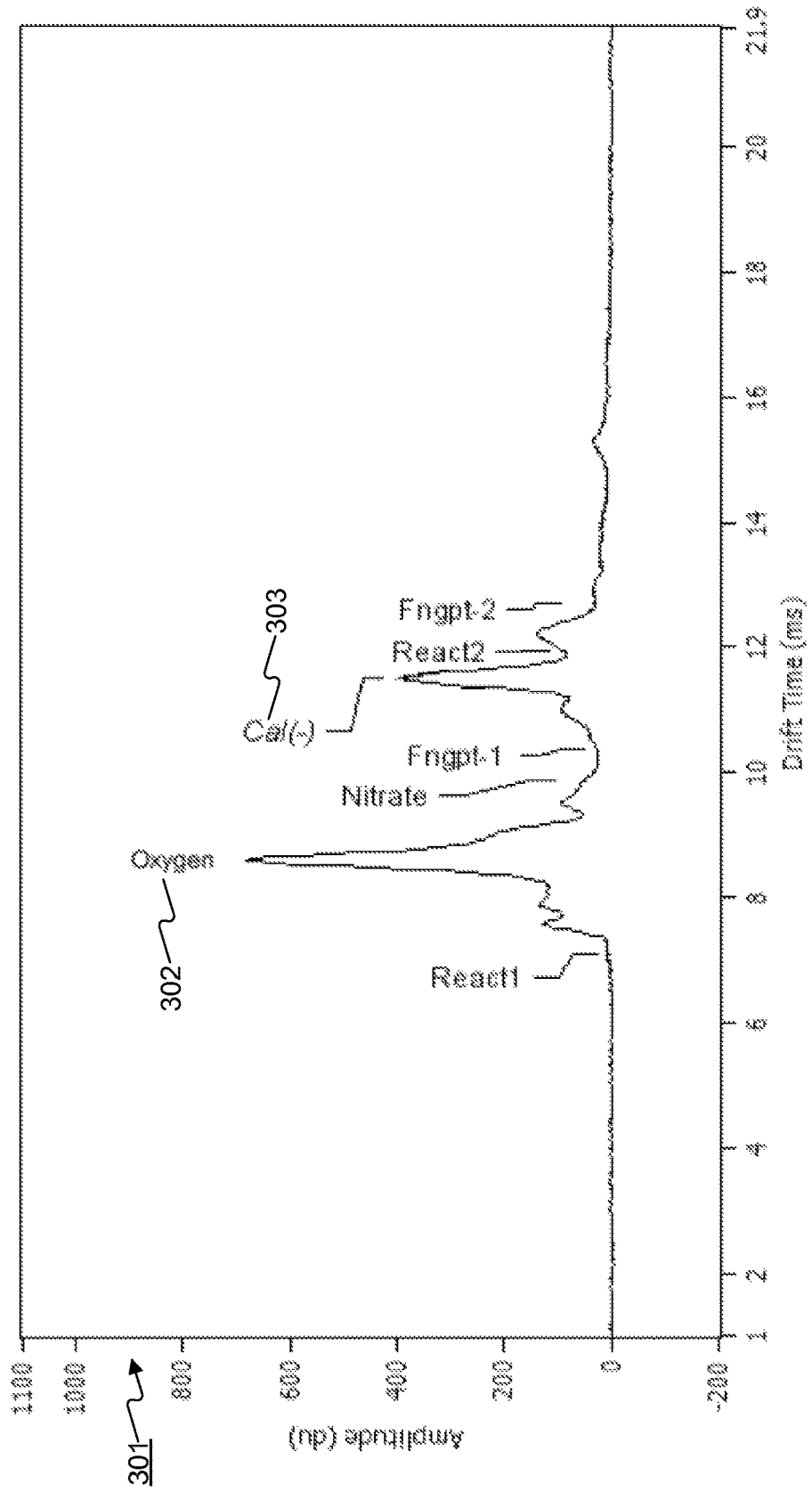
FIG. 3 depicts an example two-dimensional plasmagram associated with a second set of segment measurements of a blank swab in negative ion mode in which reactant has not been introduced into the ionization region.
Figure 4:
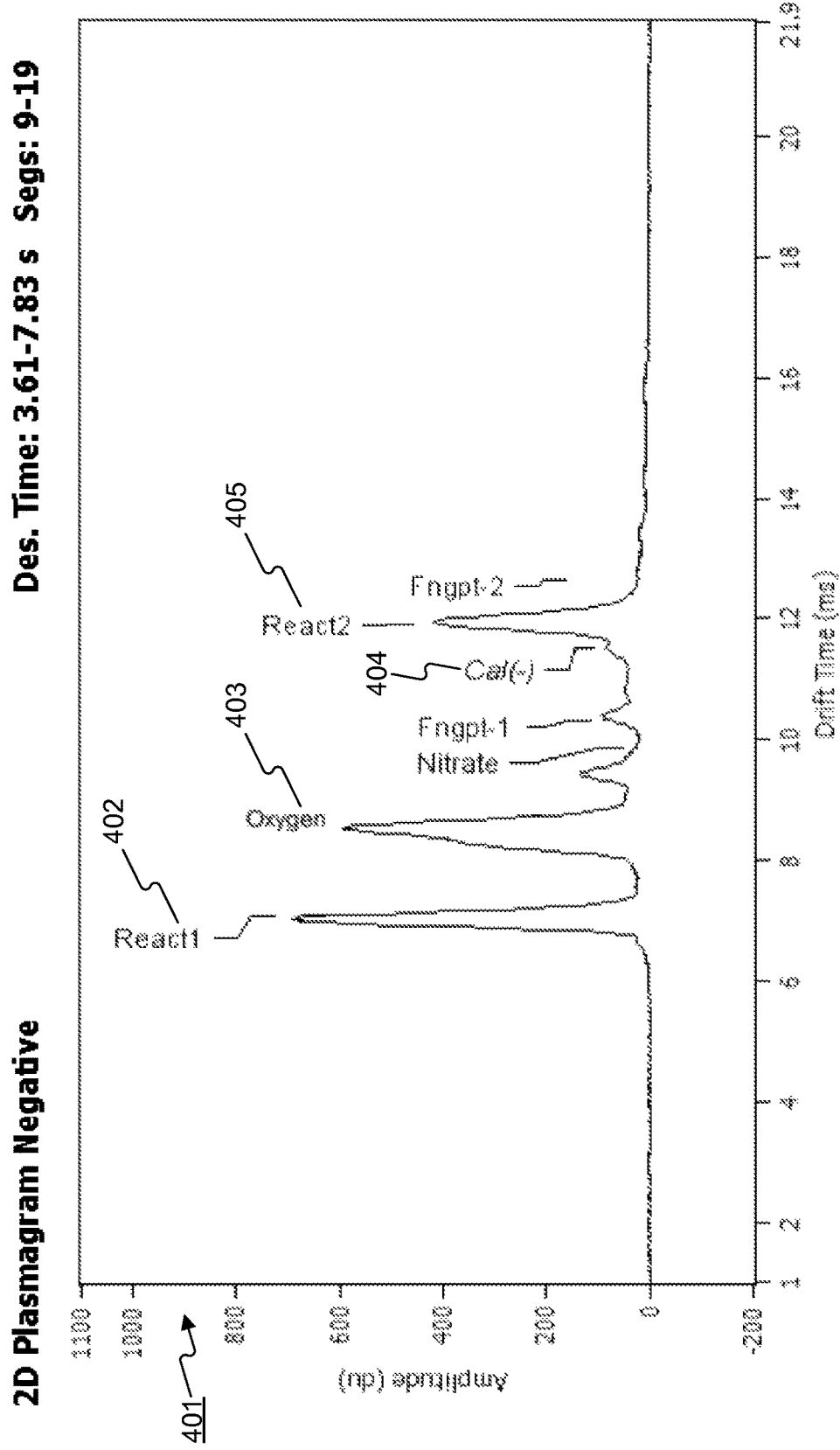
FIG. 4 depicts an example two-dimensional plasmagram associated with a third set of segment measurements of a blank swab in negative ion mode in which reactant has been introduced into the ionization region.

FIGS. 2-4 depict example plasmagrams associated with the current values measured at the collector 170. FIG. 2 is an example two-dimensional plasmagram 201 associated with an ion mobility spectrometer, such as ion mobility spectrometer 100, operating in positive ion mode. The abscissa of the two-dimensional plasmagram 201, the drift time, is the amount of time after the gating grid 145 opens to allow ions into the drift region 165 so that the ions can arrive at the collector 170. That is, when the ion mobility spectrometer 100 is operating in positive ion mode, the zero of the drift time abscissa corresponds to the negative voltage pulse that opens the gating grid 145. The ordinate of the two-dimensional plasmagram 201 is the current signal acquired at the collector 170 as a function of the drift time. The units associated with the ordinate of the two-dimensional plasmagram 201 can be arbitrary, as the measured current at the collector 170 can be a function of a number of design parameters associated with the construction and operation of the ion mobility spectrometer 100. As described above, a plurality of scans can be co-added together to form a segment. In the two-dimensional plasmagram 201 depicted in FIG. 2, each scan in the plurality of scans that make up a segment occurs for at least 21.9 milliseconds, and the segments numbered 1 through 4 (all in positive ion mode and occurring over 1.41 seconds of desorption time) are averaged together. Two peaks are visible in FIG. 2: a nicotinamide peak 202 (labeled in FIG. 2 as "Cal(+)") and a hydronomium peak 203.

FIG. 3 is an example two-dimensional plasmagram 301 associated with the ion mobility spectrometer 100 operating in negative ion mode. As with FIG. 2, the abscissa of the two-dimensional plasmagram 301, the drift time, is the amount of time after the gating grid 145 opens to allow ions into the drift region 165. Note, however, that when the ion mobility spectrometer 100 is operating in negative ion mode, the zero of the drift time abscissa corresponds to the positive voltage pulse that opens the gating grid 145. The ordinate of the two-dimensional plasmagram 301 is the current signal acquired at the collector 170 as a function of the drift time according to the same units associated with FIG. 2. Again, as described above, a plurality of scans can be co-added together to form a segment, and again, as described in connection with FIG. 2, each scan in the plurality of scans that make up a segment in the two-dimensional plasmagram 301, occurs for at least 21.9 milliseconds, and the segments numbered 5 through 8 (all in negative ion mode and occurring between 1.41 seconds and 3.61 seconds of desorption time) are averaged together. Several peaks are visible in FIG. 3, including an oxygen peak 302 and a nitrobenzonitrile peak 303 (labeled in FIG. 3 as "Cal(−)").

The sequence of two-dimensional plasmagrams 201 and 301 reflect a circumstance where the ion mobility spectrometer 100 has operated in positive ion mode for approximately 1.41 seconds (acquiring the data for segments 1-4), and then switched to operation in negative ion mode and starting negative ion mode scans (at approximately 1.41 seconds into desorption time). Thus, the data reflected in FIGS. 2 and 3 indicate that the ion mobility spectrometer 100 has been operating in both positive ion mode and negative ion mode, and that both dopants (nitrobenzonitrile and nicotinamide) and water are present. FIGS. 2 and 3 are part of an explosives-swab mode analysis. The two-dimensional plasmagram 401 depicted in FIG. 4 is also part of the explosives-swab mode analysis, and corresponds to an averaging of segments 9-19 acquired during desorption time 3.61 seconds to 7.83 seconds in negative ion mode. One difference between the circumstance resulting in the two-dimensional plasmagram 301 and the two-dimensional plasmagram 401 is that plasmagram 401 is associated with the presence of the reactant hexachlooroethane in the ion mobility spectrometer 100. In the two-dimensional plasmagram 401 depicted in FIG. 4, a nitrobenzonitrile peak 404 is less prominent than the oxygen peak 403 and a reactant peak 402 and a reactant peak 405.

Figure 5:
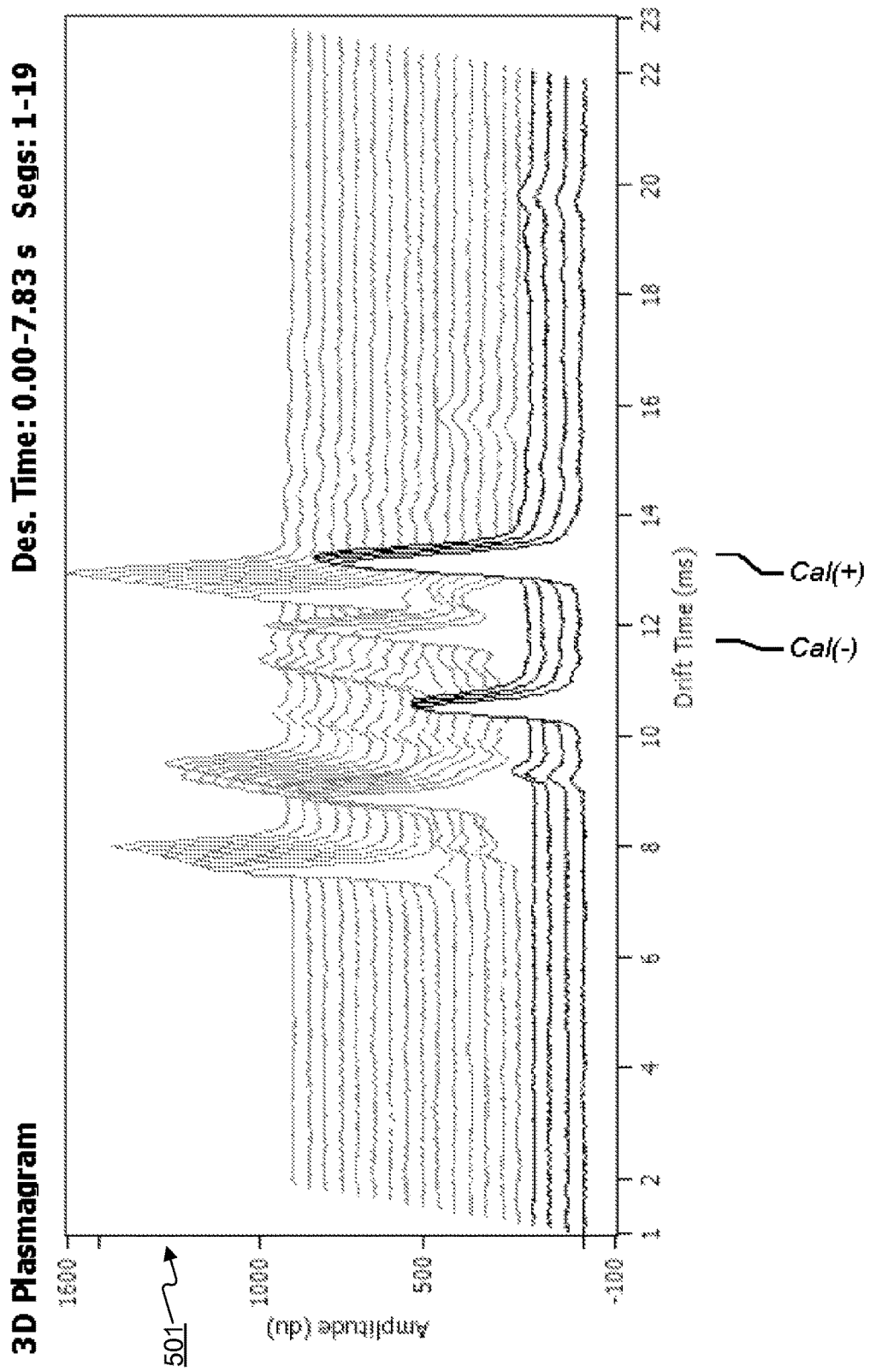
FIG. 5 depicts an example three-dimensional plasmagram associated with a first set of segment measurements in positive ion mode, negative ion mode with no reactant, and negative ion mode with reactant.

FIG. 5 depicts an exemplary three-dimensional plasmagram 501. In fact, the three-dimensional plasmagram 501 depicts segments 1-19 (acquired during desorption time 0 seconds to 7.83 seconds) corresponding to the explosives-swab mode analysis of FIGS. 2-4. The three-dimensional view depicted in FIG. 5 reflects the pattern depicted in FIGS. 2-4: positive ion mode depicted near the abscissa (segments 1-4) corresponding to the two-dimensional plasmagram 201 in FIG. 2; negative ion mode with no reactant (segments 5-8) corresponding to the two-dimensional plasmagram 301 in FIG. 3; and negative ion mode with reactant added (segments 9-19) corresponding to the two-dimensional plasmagram 401 in FIG. 4.

Figure 6:
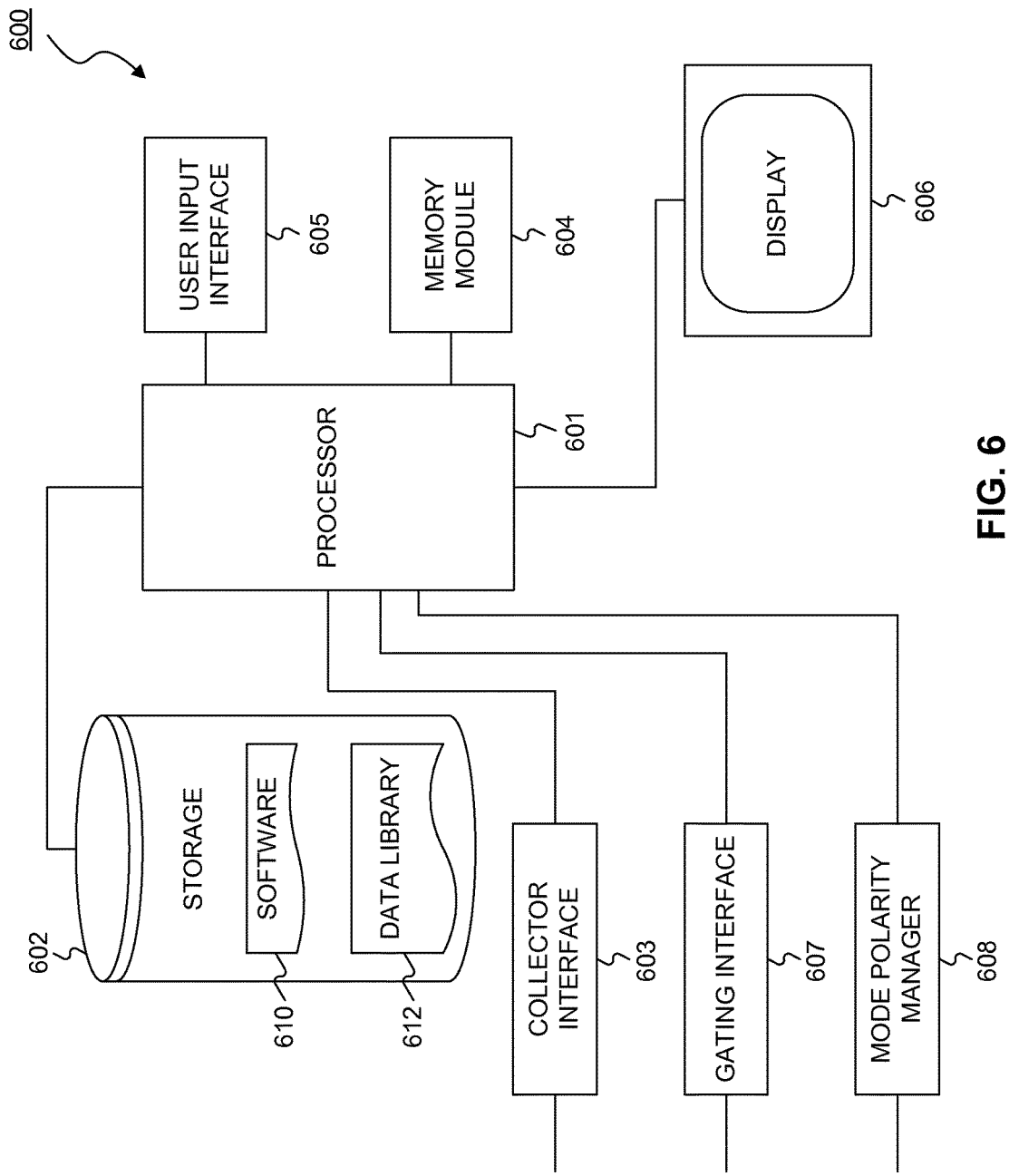
FIG. 6 depicts a data processing system consistent with an embodiment.

Consistent with an embodiment, the ion mobility spectrometer 100 includes a data processing system 600. FIG. 6 is a schematic diagram of the data processing system 600. The data processing system 600 can include a processor 601, a memory module 604, a collector interface 603, a storage 602, a user input interface 605, a display 606, a gating interface 607, and a mode polarity manager 608. The data processing system 600 can include additional, fewer, and/or different components than those listed above. The type and number of listed devices are exemplary only and not intended to be limiting.

The processor 601 can be a central processing unit ("CPU") and/or a graphic processing unit ("GPU"). The processor 601 can execute sequences of computer program instructions to perform various processes that will be explained in greater detail below. The memory module 604 can include, among other things, a random access memory ("RAM") and a read-only memory ("ROM"). The computer program instructions can be accessed and read from the ROM, the storage 602 (such as a software 610), or any other suitable memory location, and loaded into the RAM for execution by the processor 601. Although the software is depicted as being stored on storage 602, e.g., a hard drive, the instructions comprising the software may be stored in a wide variety of tangible storage media. It is the intention of this disclosure to encompass such variations. Depending on the type of data processing system 600 being used, the processor 601 can include one or more processors included on printed circuit boards, and/or microprocessor chips.

Collector interface 603 can be configured to receive signals from the collector 170 such that processor 601, for example, may store data representing the signals output by the collector in the storage 602.

The storage 602 can include any type of storage suitable for storing information. For example, the storage 602 can include one or more hard disk devices, optical disk devices, or any other storage devices that can retain the data. In an embodiment, the storage 602 can store data related to the data processing process, such as the scan data received from the collector 170, and any intermediate data created during the data processing process. The storage 602 can also include analysis and organization tools for analyzing and organizing the information contained therein, such as a data library 612 that can include data associated with plasmagram peak positions, peak amplitudes, peak widths, and/or reduced ion mobility values. In addition, the gating interface 607, via the hardware included in the data processing system can be configured to provide a signal, such as a pulse, to open the gating grid 145.

A user may implement the user input interface 605 to input information into the data processing system 600, and can include, for example, a keyboard, a mouse, a touch screen, and/or optical or wireless computer input devices (not shown). The user can input control instructions via user input interface 605 to control the operation of the ion mobility spectrometer 100. For example, the user can input parameters to adjust the operation of the data processing system 600 and/or the ion mobility spectrometer.

The mode polarity manager 608 can be configured to manage the various voltages associated with components of the ion mobility spectrometer 100, such as the repelling grid 125, the fixed grid 135, the gating grid 145 (in closed mode, for example), the drift rings 160, and the guard grid 175. The mode polarity manager 608, can be configured to control when and in what order the various components change polarities as the ion mobility spectrometer 100 changes modes.

One or more modules of the data processing system 600 can be used to implement, for example, a determination of certain characteristics of plasmagram peaks and whether the characteristics are within predetermined and/or derived ranges. Further, one or more modules of the data processing system 600 disclosed consistent with FIG. 6 can be used to implement a method for normalizing plasmagram data as described below. Further, the storage 602 can be used, for example, to store data relating to a detection library (such as in the data library 612), which can include characteristics of plasmagram peaks of known materials and/or other data such as reduced ion mobility values. The storage 612 can also be used, for example, to store timing information relating to switching frequencies or clear-down periods consistent with embodiments of the present disclosure.

Molecules and atoms that are analyzed by the ion mobility spectrometer 100 can, from time to time, generate a large peak in a plasmagram. Following such events, residual sample, such as molecules, atoms, and/or ions associated with the creation of that peak can remain in the ionization region 140 or elsewhere in the ion mobility spectrometer 100. The process of removing these residual materials can be referred to as "fast clearing down." A fast clear-down operation can be achieved by rapidly switching the ion mobility spectrometer 100 from positive ion mode to negative ion mode. Exemplary time ranges for operation in one mode (i.e., one of positive ion mode and negative ion mode) before switching to the other mode to expedite clear-down can be less than approximately 1 second. For example, in one fast clear-down mode, the ion mobility spectrometer 100 can operate in positive ion mode for approximately 20 milliseconds before switching to negative ion mode. In fast clear-down mode, no sample may be introduced so the ion mobility spectrometer can remove residual sample introduced before receipt of a clear-down trigger. That is, the ion mobility spectrometer 100 can operate in positive ion mode consistent with one scan period before switching to negative ion mode. In a further fast-switching clear-down mode, the ion mobility spectrometer 100 can operate in positive ion mode for approximately 1 second before switching to negative ion mode. Under this clear-down mode, the ion mobility spectrometer 100 can operate in positive ion mode consistent with 40 scan periods before switching to negative ion mode.

As described above, a number of circumstances can trigger a fast clear-down. For example, clear down can be triggered when certain ions of interest such as ions corresponding to explosives or contraband drugs are detected by the collector 170. Such ions can have the capacity to persist in the ionization region 140. If, for example, the ionization region 140 is not cleared of these ions, then subsequent readings can be contaminated and yield inaccurate results. In this way, the ion mobility spectrometer can fast clear-down in order to purge sample residue, e.g., ions corresponding to the sample, left from previous operation (e.g., run) that may remain in the ionization region 140.

In one embodiment, the ion mobility spectrometer 100 in fast-switching clear-down mode can acquire current information from the collector 170 during the fast clear-down operation to determine if a detected plasmagram amplitude associated with a residual ion persists. If the acquired current information indicates that a plasmagram amplitude associated with a residual ion persists, then that information can be an indication that further fast-switching clear-down operation may be warranted. In an additional embodiment, the ion mobility spectrometer 100 in fast-switching clear-down mode can operate in fast clear-down mode for a time period that can be predetermined based upon detected or preset criteria. For example, the ion mobility spectrometer 100 can be configured to operate in fast clear-down mode for approximately two minutes. The predetermined time period can be based upon the particular state of the ion mobility spectrometer 100, or can be based upon a clear-down trigger as described herein.

In another embodiment, clear down can be triggered when the ion mobility spectrometer 100 is being powered on or powered off. Clearing down the ionization region 140 and drift region 165 just prior to and/or after a period of non-use can assist in the maintenance of the ion mobility spectrometer 100.

In another embodiment, fast clear down can be triggered periodically during operation of the ion mobility spectrometer 100. For example, the fast clear down operation can trigger automatically every hour, or more or less frequently, depending on preference.

In another embodiment, clear down can be triggered when the ion mobility spectrometer 100 detects either the presence or absence of particular plasmagram peaks. The presence of plasmagram peaks corresponding to contaminants such as sorbitols, nitrates, or fingerprint oils can trigger fast clear-down. The absence of peaks corresponding to a known dopant or calibrant, for example, could trigger clear down because their absence can be an indication that the ion mobility spectrometer 100 is not operating in accordance with specifications. In positive ion mode, water is a substance may be present in the ionization region 140. In negative ion mode, oxygen is a substance may be present in the ionization region 140. Therefore, the absence of either of these substances during a test under the respective mode could trigger a clear down operation.

Fast Clear down operation can be triggered by the detection by the ion mobility spectrometer 100 and associated data processing system including software of any plasmagram peak which exceeds predetermined ranges for characteristics such as amplitude or intensity.

Figure 7:
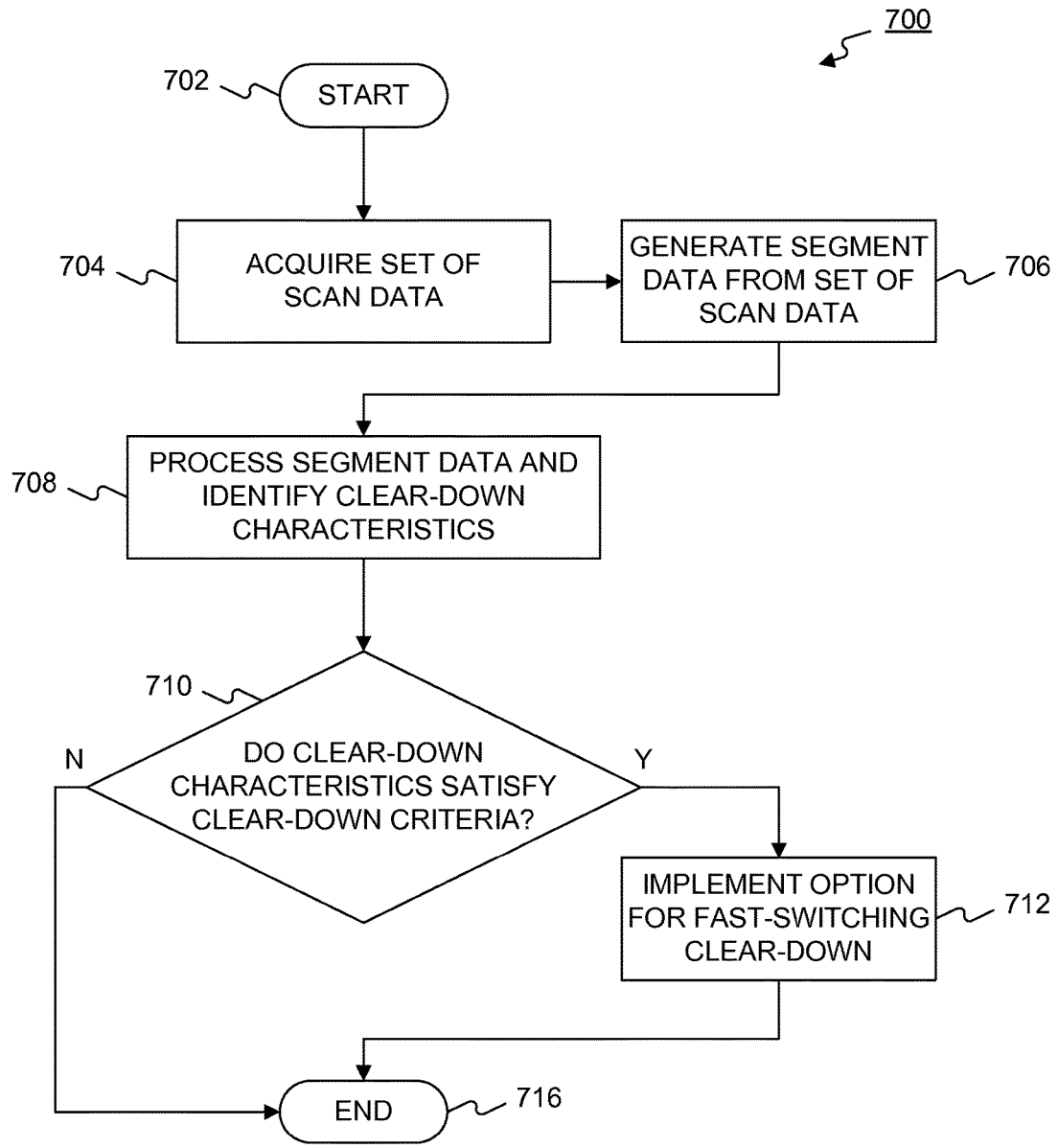
FIG. 7 is a flowchart depicting a method of clearing-down an ion mobility spectrometer consistent with an embodiment.

In one embodiment, illustrated in FIG. 7, the ion mobility spectrometer 100 can be operated in fast clear-down mode upon acquiring a signal that satisfies certain parameters, such as exceeding a certain size, occurring at a certain position, and/or exceeding a certain width. Such a signal can indicate the presence of a residual molecule, atom, and/or ion in the ion mobility spectrometer 100.

Step 704 corresponds to the acquisition of scan data by the ion mobility spectrometer 100. Data corresponding to a single scan can be acquired by operation of the ion mobility spectrometer in either positive ion mode or negative ion mode as described above. In addition, as has been discussed earlier, an exemplary time period for such a single scan can be 25 milliseconds. A set of scan data can correspond to a plurality of such scans. Data corresponding to the scan data acquired in step 704 can be conveyed to the processor 601 through the collector interface 603.

In step 706, segment data is generated from the set of scan data acquired in step 704. For example, a plurality of scans can be co-added to form a single segment. The operation associated with step 706 can reduce the signal-to-noise associated with the acquisition of scan data and can be performed by the processor 601 in accordance with instructions loaded into the memory module 604 from the storage 602.

In step 708, the segment data generated in step 706 can be processed by the processor 601 to identify any characteristics of the segment data that may correspond to a clear-down trigger. This operation can be performed by the processor 601 in accordance with signal processing instructions loaded into the memory module 604 from the storage 602. Without limitation, characteristics of the segment data generated by the ion mobility spectrometer 100 that can serve as the basis for triggering a clear-down operation. Examples include, but are not limited to an amplitude of a peak in the segment data at a particular drift time in positive ion mode or negative ion mode, a full-width-half-maximum of a peak in the segment data at a particular drift time (in positive ion mode or negative ion mode), and an integral of a peak in the segment data at a particular drift time (again in positive ion mode or negative ion mode).

In step 710, processor 601 can determine whether any of the clear-down characteristics identified in step 708 satisfy criteria or conditions to generate a clear-down trigger. The data library 612 can contain a collection of information relating to such criteria or conditions. For example, the data library 612 can include a data collection, stored in a lookup table or some other tabular form, a plurality of drift times cross-referenced to peak amplitudes, peak FWHM, peak integrals, positive ion mode or negative ion mode, reduced ion mobility values, etc.

For example, ions associated with explosives or narcotics can persist in the ion mobility spectrometer 100 after they have been introduced for analysis, and can thereby generate both a large initial signal and a residual signal that can interfere with subsequent analysis by the ion mobility spectrometer 100. Accordingly, at step 710, processor 601 can determine whether the generated segment data according to one of a positive ion mode or a negative ion mode exhibits a peak at a drift time corresponding to an ion associated with a target substance, such as TNT or cocaine. If the segment data indicates the presence of such a peak in the appropriate ion mode, and the peak has a relative amplitude that exceeds a specified detection threshold (e.g., three times the detection threshold at that position) processor 601 can generate a clear-down trigger. Consistent with the current disclosure, other criteria sufficient to generate a clear-down trigger can include a peak in the appropriate ion mode where the FWHM of the peak exceeds a specified threshold (e.g., 1.5 times an expected peak at that drift time), and/or a peak in the appropriate ion mode where the integral of the peak over a drift time exceeds a specified threshold that, for example, may be three times that of the detection threshold for a peak at that drift time position. Other criteria that might serve as a clear-down trigger include the lack of detection of an expected peak, such as a peak associated with a dopant, a calibrant, water, or oxygen, or a particular result of a health check operation.

If processor 601 determines that the characteristics associated with the segment data do not satisfy the clear-down criteria, then the ion mobility spectrometer 100 can continue operation without clear-down (indicated by step 716). Alternatively, if processor 601 determines that the characteristics associated with the segment data do satisfy the clear-down criteria, then a clear-down trigger can be generated and ion mobility spectrometer 100 can implement an option for fast clear-down, which is reflected in step 712. For example, ion mobility spectrometer 100 can be configured to provide an indication to a user, through the display 606, that a clear-down operation may be warranted. The ion mobility spectrometer 100 can provide as an option to the user the ability to select the clear-down option and implement the fast-switching clear-down. For example, upon notification to the user through the display 606, the user interface 605 can be configured to accept a selection by the user to either implement the fast clear-down process, or to not implement the fast-switching clear-down process. Upon selection of the fast-switching clear-down option by the user, the ion mobility spectrometer 100 can be configured to implement fast clear-down.

In one embodiment, fast clear-down can be managed by the processor 601 and the mode polarity manager 608, where the gating grid 145 is maintained in a closed configuration (as described further below), and a set number of changes from one polarity mode to the other polarity mode are implemented at a set frequency. Alternatively, and without limitation, fast clear-down can be accomplished by maintaining the gating grid 145 in a closed configuration, and by triggering changes from one polarity mode to another polarity mode at a set frequency for a set period of time—again, which can be implemented by the processor 601 and mode polarity manager 608.

For example, the processor 601 and mode polarity manager 608 can manage a fast clear-down mode by generating instructions and controlling the voltages on the ion mobility spectrometer 100 such that the ion mobility spectrometer 100 alternates between positive ion mode to negative ion mode at a period of about 25 milliseconds and continues such alternating for about two minutes. The switching can take approximately 2 milliseconds. The time period after switching and before the voltages reach equilibrium can be less than about 5 millseconds. Where a separate processor manages the fast-clear-down process, processor 601 can generate a clear-down trigger for such processor.

Figure 8:
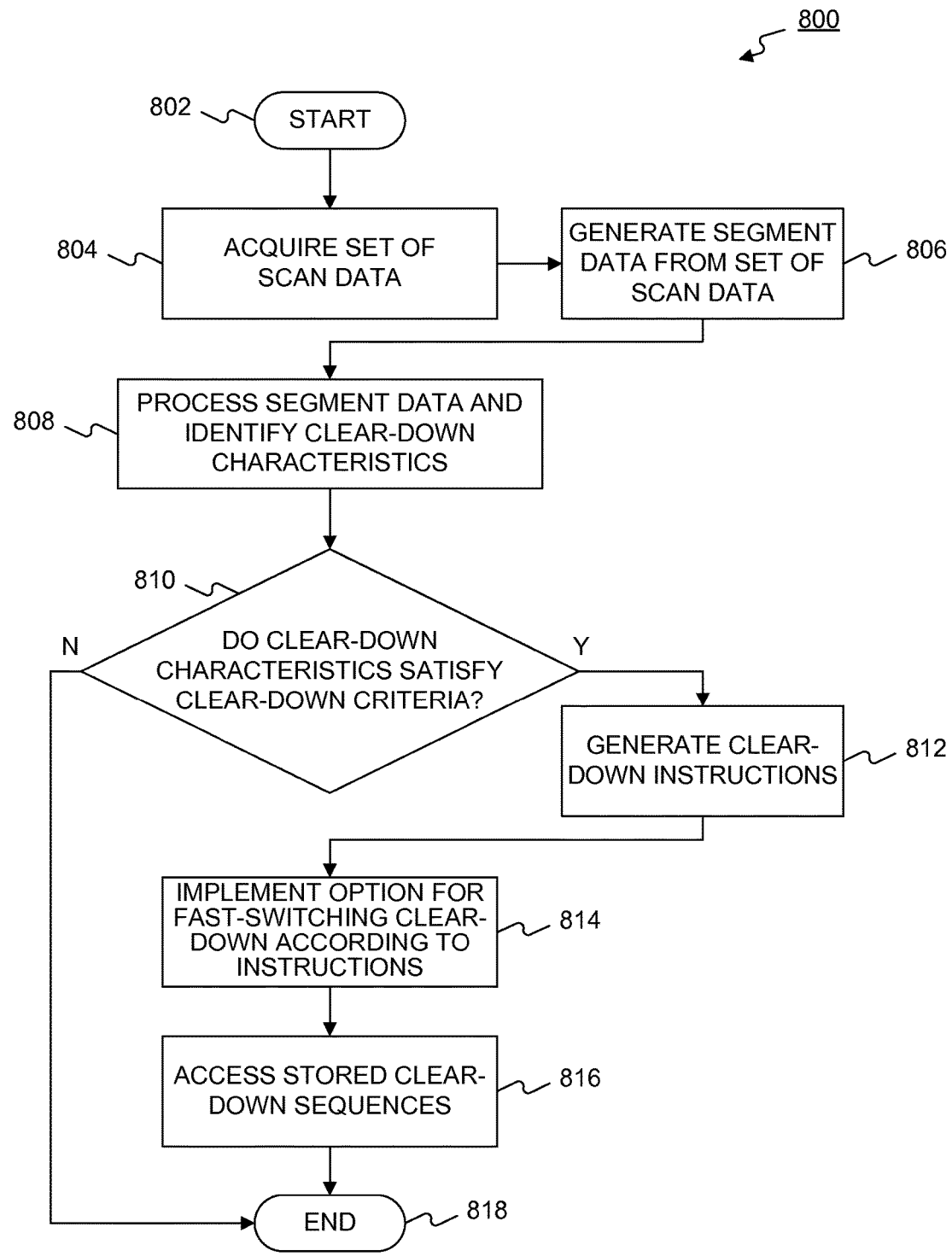
FIG. 8 is a flowchart depicting a method of clearing-down an ion mobility spectrometer consistent with an embodiment.

In a further embodiment consistent with the current disclosure, and depicted in FIG. 8, processor 601 may tailor fast clear-down instructions depending upon the particular clear-down characteristics that are present in the segment data. Again, as has been described in connection with FIG. 7, step 804 corresponds to the acquisition of scan data by the ion mobility spectrometer 100. Data corresponding to a single scan can be acquired by operation of the ion mobility spectrometer in either positive ion mode or negative ion mode as described above, e.g., 25 milliseconds. A set of scan data can correspond to a plurality of such scans. Data corresponding to the scan data acquired in step 804 may be conveyed to the processor 601 through the collector interface 603.

In step 806, segment data is generated from the set of scan data acquired in step 804. For example, a plurality of scans can be co-added to form a single segment. The operation associated with step 806 can reduce the signal-to-noise associated with the acquisition of scan data and can be performed by the processor 601 in accordance with instructions loaded into the memory module 604 from the storage 602.

In step 808, the segment data generated in step 806 can be processed to identify any characteristics of the segment data that may correspond to a clear-down trigger. Without limitation, characteristics of the segment data generated by the ion mobility spectrometer 100 that can result in a trigger for a clear-down operation can be the amplitude of a peak in the segment data at a particular drift time in positive ion mode or negative ion mode, the full-width-half-maximum of a peak in the segment data at a particular drift time (in positive ion mode or negative ion mode), and the integral of a peak in the segment data at a particular drift time (again in positive ion mode or negative ion mode).

In step 810, processor 601 can determine whether any of the clear-down characteristics identified in step 808 satisfy criteria or conditions to generate a clear-down trigger. The data library 612 can contain a collection of information relating to such criteria or conditions. For example, the data library 612 may include a data collection, stored in a lookup table or some other tabular form, a plurality of drift times cross-referenced to peak amplitudes, peak FWHM, peak integrals, positive ion mode or negative ion mode, reduced ion mobility values, etc.

For example, and as has been discussed above, ions associated with explosives or narcotics can persist in the ion mobility spectrometer 100 after they have been introduced for analysis, and can thereby generate both a large initial signal and a residual signal that can interfere with subsequent analysis by the ion mobility spectrometer 100. Accordingly, at step 810, processor 601 can determine whether the generated segment data according to one of a positive ion mode or a negative ion mode exhibits a peak at a drift time corresponding to an ion associated with a target substance, such as TNT or cocaine. If the segment data indicates the presence of such a peak in the appropriate ion mode, and the peak has a relative amplitude that exceeds a specified threshold. Other criteria sufficient to generate a clear-down trigger can include, but are not limited to, a peak in the appropriate ion mode where the FWHM of the peak exceeds a specified threshold and/or a peak in the appropriate ion mode where the integral of the peak over a drift time exceeds a specified threshold that, for example, may be defined as three times the detection threshold for a peak at that drift time position. Other criteria that might serve as a clear-down trigger include absence of an expected peak, such as a peak associated with a dopant, a calibrant, water, or oxygen; or a particular result of a health check operation.

If processor 601 determines that the characteristics associated with the segment data do not satisfy the clear-down criteria, then the ion mobility spectrometer 100 can continue operation without clear-down (indicated by step 818). Alternatively, if processor 601 determines that the characteristics associated with the segment data do satisfy the clear-down criteria, then specific clear-down instructions associated with the detected characteristics can be generated and the ion mobility spectrometer 100 can implement an option for fast-switching clear-down according to these instructions. In step 812, processor 601 can generate specific clear-down instructions.

For example, it can be determined that, where the amplitude of the peak associated with TNT is determined to be more than three times a stored or derived value, the residual presence of TNT in the ion mobility spectrometer 100 can be removed by maintaining the gating grid 145 in a closed state, and by alternating between positive ion mode and negative ion mode at a frequency of 30 Hz for about 2 minutes. Alternatively, where the amplitude of the peak associated with cocaine is determined to be about three times a stored value it can be determined that the residual presence of cocaine in the ion mobility spectrometer 100 can be removed by maintaining the gating grid 145 in a closed state and by alternating between positive ion mode and negative ion mode at a frequency of 10 Hz for about 1 minute. Accordingly, depending upon the value of the clear-down characteristics, processor 601 can generate specialized clear-down instructions. Alternatively, particular sequences of mode polarity switching (i.e., a frequency of switching and a total duration) can be stored in storage 602, and the clear-down instructions generated by the processor 601 can comprise the address in storage 602 memory associated with the stored sequence. Although the exemplary fast-switching clear-down sequences described above relate to a single frequency (e.g., 30 Hz or 10 Hz) for a particular duration (e.g., 2 minutes or 1 minute) such sequences are exemplary only and are not limiting. It can be determined, for example, that a variation in frequency can be useful for clearing-down ion mobility spectrometer 100 consistent with the current disclosure. Again, by way of example only and without limitation, a particular fast clear-down sequence can include alternating between positive ion mode and negative ion mode at a relatively high frequency (e.g., 40 Hz) and, over a time of about two minutes, transitioning such a high frequency switching to a lower frequency switching (e.g., over the course of two minutes, reducing the frequency of alternating between positive ion mode and negative ion mode from about 40 Hz to about 1 Hz). It can also be determined that a clear-down sequence should be available that exhibits no regular frequency. That is, the amount of time spent in positive ion mode before switching to negative ion mode may not exhibit any regularity (from the standpoint of time periods) over two or more consecutive polarity switches.

In step 814, processor 601 can implement an option for fast clear-down. For example, ion mobility spectrometer 100 can be configured to provide an indication to a user, through the display 606, that a clear-down operation may be warranted. The ion mobility spectrometer 100 can provide as an option to the user the ability to select the clear-down option and implement the fast clear-down. For example, upon notification to the user through the display 606, the user interface 605 can be configured to accept a selection by the user to either implement the fast-clear-down process, or to not implement the fast clear-down process. Upon selection of the fast clear-down option by the user, the ion mobility spectrometer 100 can be configured to implement fast clear-down.

According to step 816, a processor 601 and mode polarity manager 608 can access the stored clear-down sequences as desired. Again, where a separate processor manages the fast clear-down process, processor 601 can generate a clear-down trigger for such a processor, and the processor can access stored sequences as desired.

In another embodiment depicted in FIG. 9, scan data and segment data can be acquired and processed during the fast-switching clear-down mode operation, and fast-switching clear-down mode can continue until data associated with any residual signal (such as a peak amplitude, FWHM, and/or integral of peak area) indicates that the residual signal has dropped below a threshold. Such thresholds can vary based on the ion which is associated with the residual signal. Similar to the peak characteristics discussed above, such thresholds can be in the data library 612, which can include data relating to potential detected ions and their corresponding drift times, along with corresponding clear-down threshold values.

Figure 9:
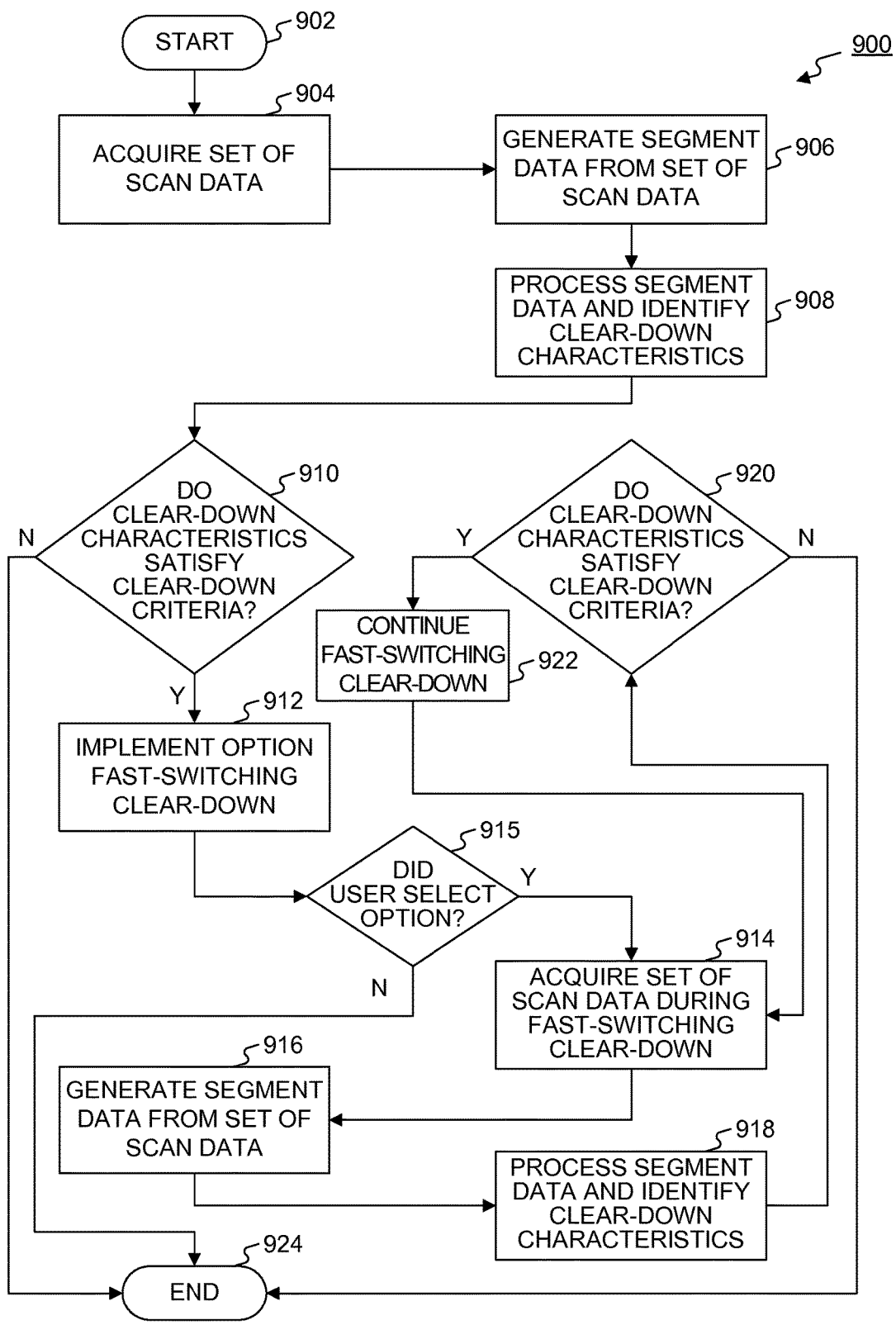
FIG. 9 is a flowchart depicting a method of clearing-down an ion mobility spectrometer consistent with an embodiment.

In FIG. 9, step 904 corresponds to the acquisition of scan data by the ion mobility spectrometer 100. Again, data corresponding to a single scan can be acquired by operation of the ion mobility spectrometer in either positive ion mode or negative ion mode as described above. In addition, as has been discussed earlier, an exemplary time period for such a single scan can be 25 milliseconds. A set of scan data can correspond to a plurality of such scans. Data corresponding to the scan data acquired in step 904 may be conveyed to the processor 601 through the collector interface 603.

In step 906, segment data is generated from the set of scan data acquired in step 904. For example, a plurality of scans can be co-added to form a single segment. The operation associated with step 906 can reduce the signal-to-noise associated with the acquisition of scan data and can be performed by the processor 601 in accordance with instructions loaded into the memory module 604 from the storage 602.

In step 908, the segment data generated in step 906 can be processed by the processor 601 to identify any characteristics of the segment data that may correspond to a clear-down trigger. Again, this operation can be performed by the processor 601 in accordance with signal processing instructions loaded into the memory module 604 from the storage 602. Without limitation, characteristics of the segment data generated by the ion mobility spectrometer 100 that can result in a trigger for a clear-down operation can be the amplitude of a peak in the segment data at a particular drift time in positive ion mode or negative ion mode, the full-width-half-maximum of a peak in the segment data at a particular drift time (in positive ion mode or negative ion mode), and the integral of a peak in the segment data at a particular drift time (again in positive ion mode or negative ion mode).

In step 910, processor 601 can determine whether any of the clear-down characteristics identified in step 908 satisfy criteria or conditions to generate a clear-down trigger. The data library 612 can contain a collection of information relating to such criteria or conditions. For example, the data library 612 may include a data collection, stored in a lookup table or some other tabular form, a plurality of drift times cross-referenced to peak amplitudes, peak FWHM, peak integrals, positive ion mode or negative ion mode, reduced ion mobility values, etc.

For example, ions associated with explosives or narcotics can persist in the ion mobility spectrometer 100 after they have been introduced for analysis, and can thereby generate both a large initial signal and a residual signal that can interfere with subsequent analysis by the ion mobility spectrometer 100. Accordingly, at step 910, processor 601 can determine whether the generated segment data according to one of a positive ion mode or a negative ion mode exhibits a peak at a drift time corresponding to an ion associated with a target substance, such as TNT or cocaine. If the segment data indicates the presence of such a peak in the appropriate ion mode, and the peak has a relative amplitude that exceeds a specified threshold that, for example, may be defined as approximately three times that of the detection threshold for a peak at that position, processor 601 can generate a clear-down trigger. Other criteria sufficient to generate a clear-down trigger can include a peak in the appropriate ion mode where the FWHM of the peak exceeds a specified threshold that, for example, may be defined as 1.5 times that of an expected peak at that drift time position, and/or a peak in the appropriate ion mode where the integral of the peak over a drift time exceeds a specified threshold that, for example, may be defined as three times that of the detection threshold for a peak at that drift time position. Other criteria that might serve as a clear-down trigger include the lack of detection of an expected peak, such as a peak associated with a dopant, a calibrant, water, or oxygen; or a particular result of a health check operation.

If the processor 601 determines that the characteristics associated with the segment data do not satisfy the clear-down criteria, then the ion mobility spectrometer 100 can continue operation without clear-down (indicated by step 924). Alternatively, if processor 601 determines that the characteristics associated with the segment data do satisfy the clear-down criteria, then specific clear-down instructions associated with the detected characteristics can be generated and the ion mobility spectrometer 100 can implement an option for fast clear-down according to these instructions.

In step 912, processor 601 can implement an option for fast-switching clear-down. For example, ion mobility spectrometer 100 can be configured to provide an indication to a user, through the display 606, that a clear-down operation may be warranted. The ion mobility spectrometer 100 can provide as an option to the user the ability to select the clear-down option and implement the fast clear-down. For example, the user interface 605 can be configured to accept a selection by the user to either implement the fast-switching clear-down process, or to not implement the fast clear-down process. Upon selection of the fast clear-down option by the user (step 915), the ion mobility spectrometer 100 can be configured to implement fast clear-down.

According to step 914, the ion mobility spectrometer 100 can acquire scan data during fast-switching clear-down. Accordingly, voltage pulses can be sent the gating grid 145 to open the gating grid 145 at scan period intervals. In addition, scan data can be acquired from the collector 170. Upon the acquisition of one or more sets of scan data, in step 916 the processor 601 can generate segment data from the scan data acquired in step 914. Note that if there is only one set of scan data acquired in step 914, the segment data generated in step 916 and the scan data acquired in step 914 can be identical. In step 918, the segment data can be processed by the processor 601 to determine whether the segment data includes any clear-down characteristics. At step 920, processor 601 can compare the clear-down characteristics identified in step 918 and determine whether there is any remaining residual signal. If there is no remaining residual signal, then fast-switching clear-down mode can conclude, as indicated by step 924. Otherwise, the ion mobility spectrometer 100 can continue in fast clear-down mode (step 922). The loop represented by steps 922, 914, 916, 918, and 920 can continue until any residual signal acquired during the fast clear-down process drops below a threshold. Again, where a separate processor manages the fast-switching clear-down process, processor 601 can generate a clear-down trigger for such a processor, and the processor can manage the fast clear-down process as described. The fast clear-down process can have some effect on the values measured by the collector 170. These effects are described below, as are systems and methods that can be used to address these effects.

Figure 10:
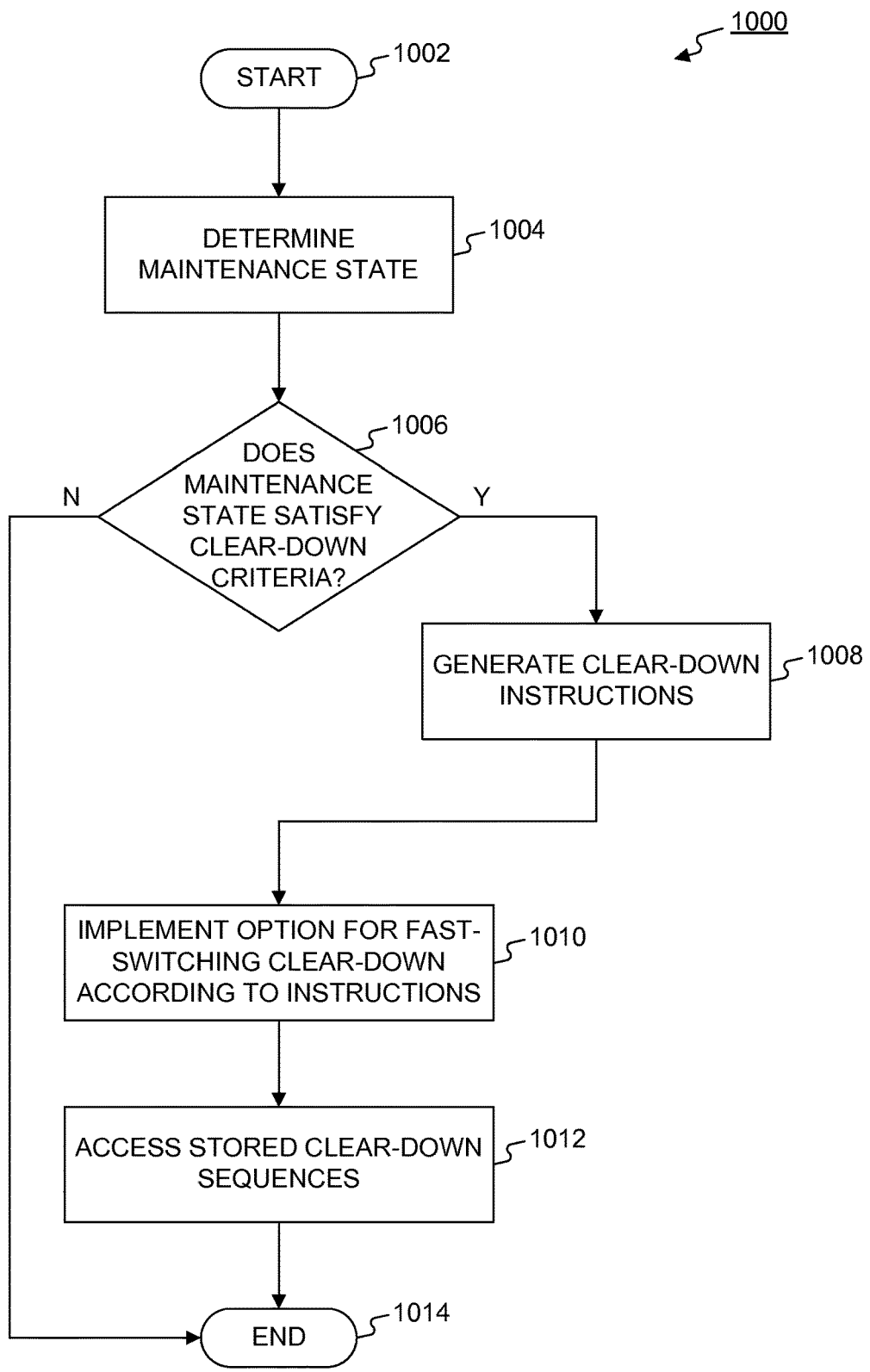
FIG. 10 is a flowchart depicting a method of clearing-down an ion mobility spectrometer consistent with an embodiment.

In another embodiment, illustrated in FIG. 10, the ion mobility spectrometer 100 can be configured to implement a fast clear-down process according to a maintenance state of the ion mobility spectrometer 100.

In step 1004, processor 601 can determine the maintenance state of the ion mobility spectrometer 100. For example, the ion mobility spectrometer 100 can be configured to initiate a fast clear-down process upon powering up or powering down. Processor 601 can be configured to identify such a state (step 1004) and determine whether the maintenance state satisfies clear-down criteria (step 1006). If not, the ion mobility spectrometer 100 can continue operation (or power down) without implementing a fast-switching clear-down.

In the event that the maintenance state of the ion mobility spectrometer satisfies the clear-down criteria, then processor 601 can generate clear-down instructions (step 1008). The sequence of steps 1008, 1010, and 1012 can be similar to the sequence of steps described in connection with FIG. 8 (steps 812, 814, and 816). However, rather than generating specialized clear-down instructions associated with a particular signal acquired through scan data (e.g., step 812), the clear-down instructions generated in step 1008 and accessed in step 1012 can be specialized according to the maintenance state of the ion mobility spectrometer 100. For example, as described above, a power-up state or a power-down state can be associated with a particular fast clear-down sequence. Furthermore, periodic operation can also be associated with a particular fast clear-down sequence, such as providing an option to a user every hour to select a fast clear-down mode, or an option to perform the fast-switching clear-down sequence after every sample performed or after every threat detection, or alarm reported.

Fast Switching Operation

Figure 11:
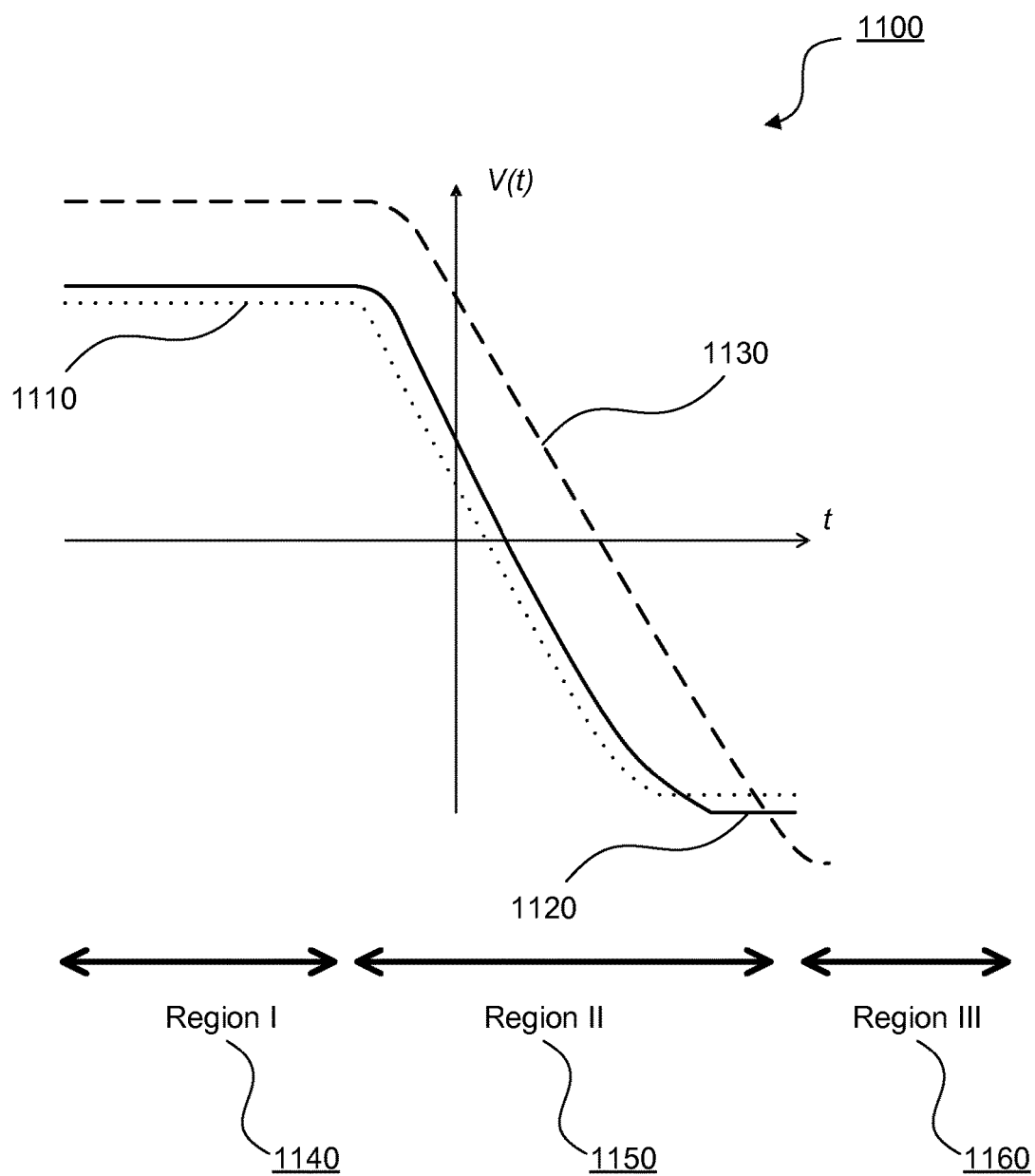
FIG. 11 depicts exemplary voltages as a function of time on the repelling grid, the gating grid, and the fixed grid of the ion mobility spectrometer of FIG. 1 during a change from positive ion mode to negative ion mode.

FIG. 11 is a plot of exemplary voltages on the repelling grid 125 (dashed curve 1130), the gating grid 145 (solid curve 1120), and the fixed grid 135 (dotted curve 1110), such as the ion mobility spectrometer 100 operating during a transition from positive ion mode (Region I 1140) to negative ion mode (Region III 1160). In Region I 1140 (positive ion mode), the voltage on the repelling grid 125 (the dashed curve 1130) is more positive than the voltage on the gating grid 145 (the solid curve 1120), which is more positive than the voltage on the fixed grid 135 (dotted curve 1110). These relative voltage magnitudes can correspond to a gating grid 145 that is closed in positive ion mode. In Region III 1160 (negative ion mode), the voltage on the repelling grid 125 (dashed curve 1130) is more negative than the voltage on the gating grid 145 (solid curve 1120), which is more negative than the voltage on the fixed grid 135 (dotted curve 1110). These relative voltage magnitudes can correspond to a gating grid 145 that is closed in negative ion mode. Between the two regions, Region I 1140 and Region III 1160, and before dotted curve 1110 (which corresponds to the voltage on the fixed grid 135) crosses solid curve 1120 (which corresponds to the voltage on the gating grid 145), dashed curve 1130 (which corresponds to the voltage on the repelling grid 125) is kept at a higher potential than both solid curve 1120 and dotted curve 1110—indicating that the voltage on the repelling grid 125 will continue to be more positive than the voltage on both of the gating grid 145 and the fixed grid 135. Accordingly, during polarity switchover in Region II 1150, when there can be negative ions present in the ionization region 140, and where the relative voltages between the gating grid 145 and the fixed grid 135 correspond to an open gate in negative ion mode, the repelling grid 125 (the dashed curve 1130) is kept high relative to the gating grid 145 (solid curve 1120). The relative voltage depicted in FIG. 11 between the repelling grid 125 and the gating grid 145 can keep the negative ions away from the gating grid 145 (and thereby the drift region 165) until after the dotted curve 1110 crosses the solid curve 1120. When dotted curve 1110 crosses solid curve 1120 and the relative voltage of the gating grid 145 is less than the voltage of the fixed grid 135, the gating grid 145 is closed in negative ion mode. After that occurs, and the gating grid 145 is closed, the magnitude of the voltage on the repelling grid 125 can pass below both the voltage of the gating grid 145 and the voltage of the fixed grid 135, thereby repelling the negative ions in the ionization region 140 towards the fixed grid 135 and the gating grid 145. In an embodiment, the time that the ion mobility spectrometer 100 spends in Region II 1150 can be approximately 2 milliseconds.

Figure 12:
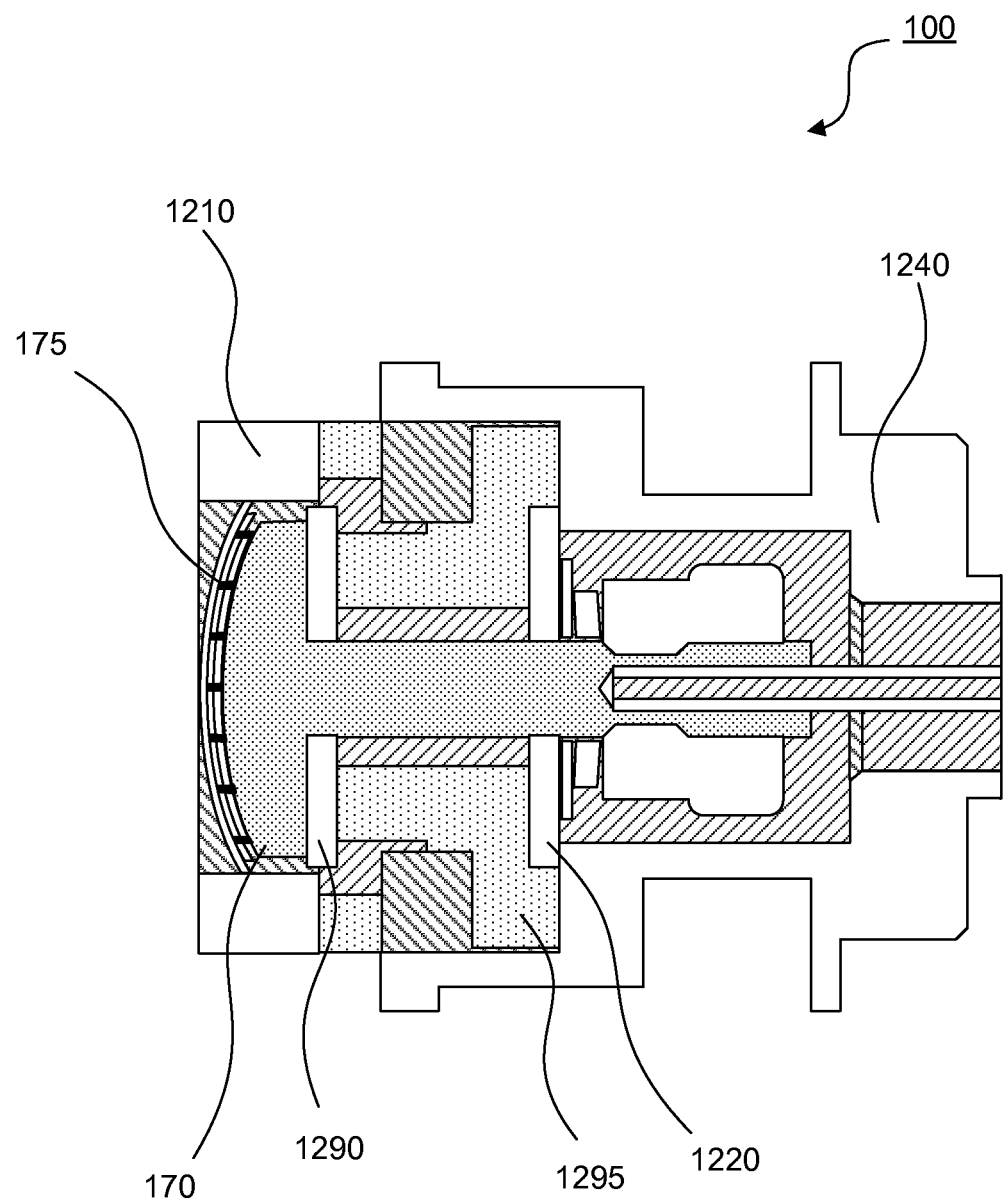
FIG. 12 is a cross sectional view of a guard grid and a collector portion of an ion mobility spectrometer consistent with an embodiment.

Although it is not depicted, a similar sequence of inverted crossings can be used consistent with the current disclosure to pass from operation in negative ion mode with a closed gating grid 145 to operation in positive ion mode with a closed gating grid 145. Again, the voltage on the repelling grid 125 can be kept low relative to the voltage of both the gating grid 145 and the fixed grid 135 until the voltage of the gating grid 145 crosses over and becomes greater than the voltage on the fixed grid 135. At that point, as has been described, the gating grid 145 has become closed in positive ion mode, and then the repelling grid 125 can cross both the voltage of the fixed grid 135 and the voltage of the gating grid 145 and create the potential gradient in the ionization region 140 that drives the positive ions towards the gating grid 145. FIG. 12 depicts a portion of a cross section of the ion mobility spectrometer 100 consistent with another embodiment. The portion of the ion mobility spectrometer 100 depicted in FIG. 12 includes the collector 170, the guard grid 175, a guard clamping ring 1210, an insulator 1290, an insulator 1220, a grounded mount 1295, and a ground shield 1240. In the embodiment depicted in FIG. 12, the insulator 1290 and the insulator 1220 can comprise ceramic material. In FIG. 12, the grounded mount 1295 can be on the opposite side of the insulator 1290 and the insulator 1220 from the collector 170. In an embodiment, the insulator 1290 and the insulator 1220 can be two washers. There can also be an insulator between the grounded mount 1295 and the guard-clamping ring 1210. This insulating material can be a thin film such as, for example, KAPTON, a polyimide film developed by DuPont. Thus, in an embodiment, there is no direct insulation (other than air) between the guard grid 175, the guard-clamping ring 1210, and the collector 170, which can reduce the effect that dielectric absorption can have on contributing to a current detected at the collector 170 during polarity switchover.

In addition, the drift region 165 can be a source of current with an output current of around 10-100 pA. Accordingly, there can be a parasitic capacitance between the collector 170 and the guard grid 175 of approximately 1 pF where the voltage between these two components can be around 90 Volts. This can result in an accumulated charge on the collector 170 (and the guard grid 175) of about 100 pC.

During a rapid polarity switch, the accumulated charge can reverse sign, such that during rapid polarity switching involving many polarity switches, the accumulated charge can be reversed many times, where the peak current (i.e., (the change in charge)/(the change in time)) can be approximately ~100 pC/1 ms~100 nA, and which can be 1,000 times larger than the typical output current from drift region 165. After a polarity switches, the voltages can stabilize in approximately 1-2 milliseconds or longer consistent with an embodiment.

A preamplifier associated with an ion mobility spectrometer can be a transimpedance amplifier that uses a high input impedance operational amplifier along with a relatively large feedback impedance (~G$\Omega$) and can be incapable of handling input currents much greater than a few hundred pA. To allow for the preamplifier associated with FIG. 2 to handle 100 nA currents associated with polarity switchovers, a parallel circuit can be implemented as indicated.

Where such a parallel circuit includes diodes connected between the input and the ground that limit the input voltage to safe value, there can remain some charge stored on the diode capacitance (and other parasitic capacitances) following a switching current that can take a relatively long time to relax and cause a distortion in the baseline of the output signal (i.e. a distortion in the plasmagram).

Figure 13:
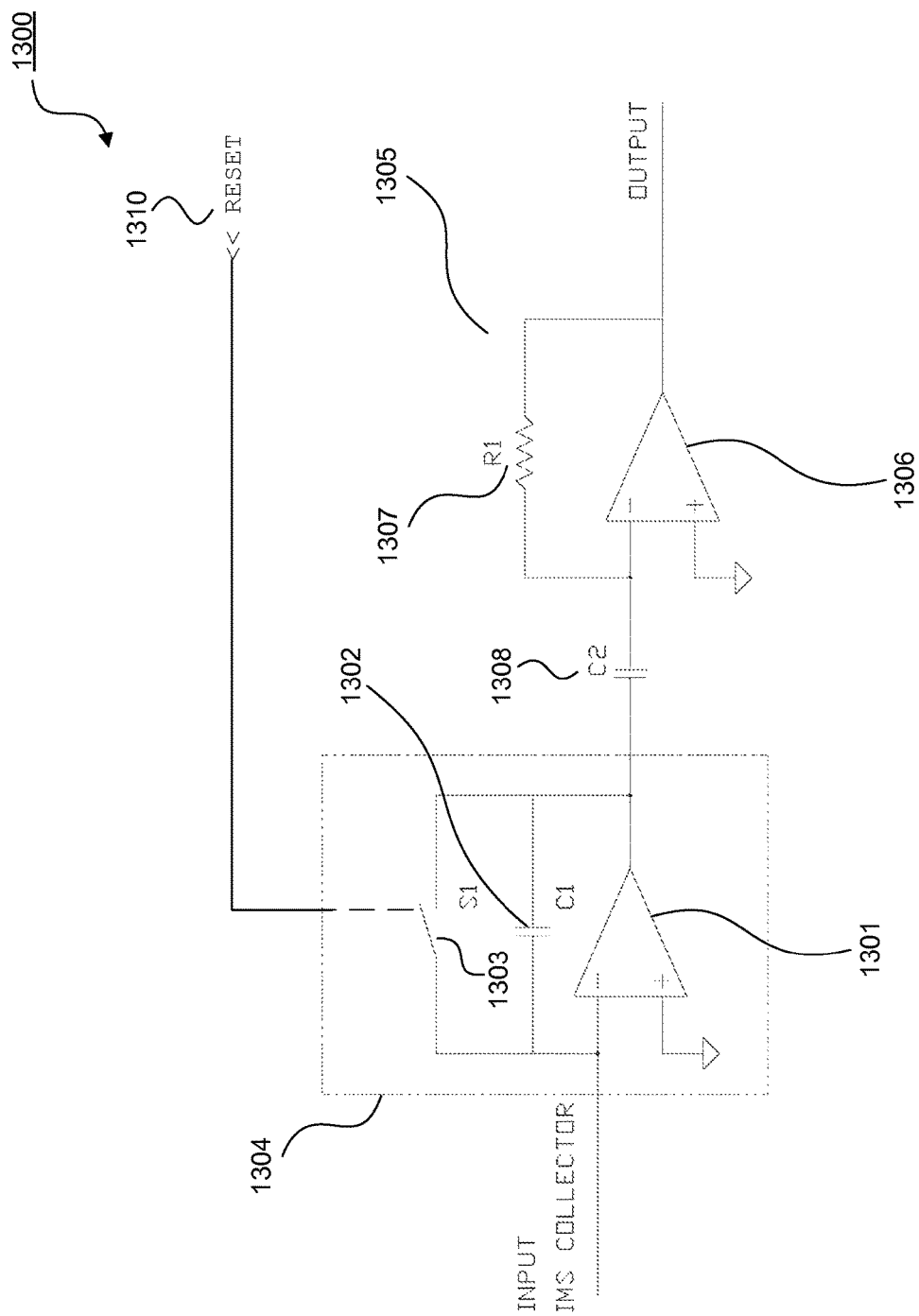
FIG. 13 is a schematic of a circuit diagram consistent with an embodiment.

FIG. 13 shows an embodiment of the preamplifier. Circuit 1300 includes a first stage 1320 (i.e., a transimpedance integrator circuit), which can include a first operational amplifier 1301, a feedback capacitor C1 1302 and a switch S1 1303. The feedback capacitor C1 1302 can be, for example, 2 pF. In an embodiment, the first operational amplifier 1301, the feedback capacitor C1 1302 and the switch S1 1303 can be available as a single integrated circuit 1304. The integrated circuit (IC) 1304 can be, for example, IVC102 manufactured by Texas Instruments. The IC 1304 can be chosen to meet a user's specifications for the switch leakage current and charge injection. Where the IC 1304 is IVC102 as described above, the manufacturer's specified input current (includes operational amplifier bias current and switch leakage) can be 0.1 pA. The charge injection can be as small as 0.2 pC. In a further embodiment, the leakage current can be much smaller than the magnitude of a signal acquired from the collector 170 (<1 pA). Because a semiconductor switch can inject a charge during opening and closing operation, the amount of charge injection associated with the low-leakage switch 1303 in an embodiment consistent with the disclosure can be selected to be below 1 pC. A second stage 1305 (i.e., a differentiator circuit) can be based around an operational amplifier 1306 which can be, for example, a low noise, precision operational amplifier such as OP27 manufactured by Analog Devices and includes a resistor R1 1307 and a capacitor C2 1308. The resistor R1 1307 can be, for example, 100 k$\Omega$, and the capacitor C2 1308 can be, for example, 22 nF. The total transimpedance (ratio of output voltage to input current) of the circuit 1300 can be given by R1·C2/C1 and may be, for example, 1 G$\Omega$. Other values for the resistor R1 1307, the capacitor C1 1302, and the capacitor C2 1308 can include, for example, about 300 k$\Omega$ for the resistor R1 1307, about 10 pF for the capacitor C1 1302, and 33 nF for the capacitor C2 1308. Generally, the values for the resistor R1 1307, the capacitor C1 1302, and the capacitor C2 1308 can depend upon the application (e.g., the desired gain).

The switch 1303 can be closed just before the start of the polarity transition, and can remain closed during fast-polarity switchover before opening a few milliseconds later when all grid voltages (such as the grid guard 175 voltage) have stabilized. Generally, the time period between the closing and the subsequent opening of the switch 1303 can be less than 5 ms. The timing of the switch 1303 can be digitally controlled by the RESET logic signal 1310, which can be generated by the processor 601. One aspect of the circuit 1300 consistent with the present disclosure is that transients introduced by the circuit 1300 can be small in magnitude, thereby avoiding contributions to distortions in the baseline of the output signal.

Figure 14:
FIG. 14 depicts a timing trace of voltage switching consistent with an embodiment.

FIG. 14 shows timing of the. Trace 1401 shows schematically the polarity of the ion mobility spectrometer 100 transitioning from positive ion mode 1411 to negative ion mode 1412 and back to positive ion mode 1413.

Trace 1402 shows the timing of a RESET signal pulse 1421, associated with RESET logic signal 1310 of switch 1303, and which can be digitally controlled by the processor 601. This can be a logic signal active LOW. It can be asserted just before the start of the ion mobility spectrometer 100 polarity transition from positive ion mode 1411 to negative ion mode 1412 and can end after all the ion mobility spectrometer 100 voltages have stabilized. Another RESET signal pulse 1422 can be asserted just before the start of the ion mobility spectrometer 100 polarity transition from negative ion mode 1412 to positive ion mode 1413. The RESET signal pulses 1421 and 1422 can last about 2 milliseconds.

Trace 1403 depicts a GATING pulse signal 1431 that can mark the beginning of the plasmagram data collection in negative ion mode 1412, and depicts a GATING pulse signal 1432 that can mark the beginning of the plasmagram data collection in positive ion mode 1413 (that is, GATING pulse signal 1432 can mark the beginning of the collection of data associated with a scan). The GATING pulses 1431 and 1432 can be configured to occur about 10 milliseconds after the ion mobility spectrometer 100 voltages have stabilized in either negative ion mode 1412 or positive ion mode 1413. This can allow for the ions within the drift region 165 of the ion mobility spectrometer 100 to establish a new equilibrium corresponding to the polarity thereby stabilizing the baseline current of the collector 170 of the ion mobility spectrometer 100.

Trace 1404 is a preamplifier output. When the RESET signal pulse 1421 is asserted, the trace 1404 can show a spike 1441 due to the discharging of capacitor C1 1302. Then, for the duration of the RESET signal pulse 1421, the output can be essentially 0 volts. At the end of the RESET signal pulse 1421, there can be a small spike 1442 due to charge injection. Then there can be a period of a few milliseconds when the ion mobility spectrometer 100 baseline current stabilizes.

Plasmagram data can be collected in scans lasting 20 to 25 milliseconds following the GATING signal pulse 1431. Depending on the implementation, the ion mobility spectrometer 100 can be operated so as to change polarity after a scan (such as oscillating between positive ion mode 1411 and negative ion mode 1412 as shown in trace 1401), or can collect several scans in one polarity before switching to the other polarity. For example, a switch of the polarity of the ion mobility spectrometer 100 can occur at any number of scans (e.g., every scan, every 5 scans, every 10 scans, or more).

When the ion mobility spectrometer 100 polarity is switched every several scans, the RESET pulse signal 1421 may be asserted after each scan and released before each GATING pulse signal 1431 or every several scans as long as the IC 1304 does not saturate.

Figure 16:
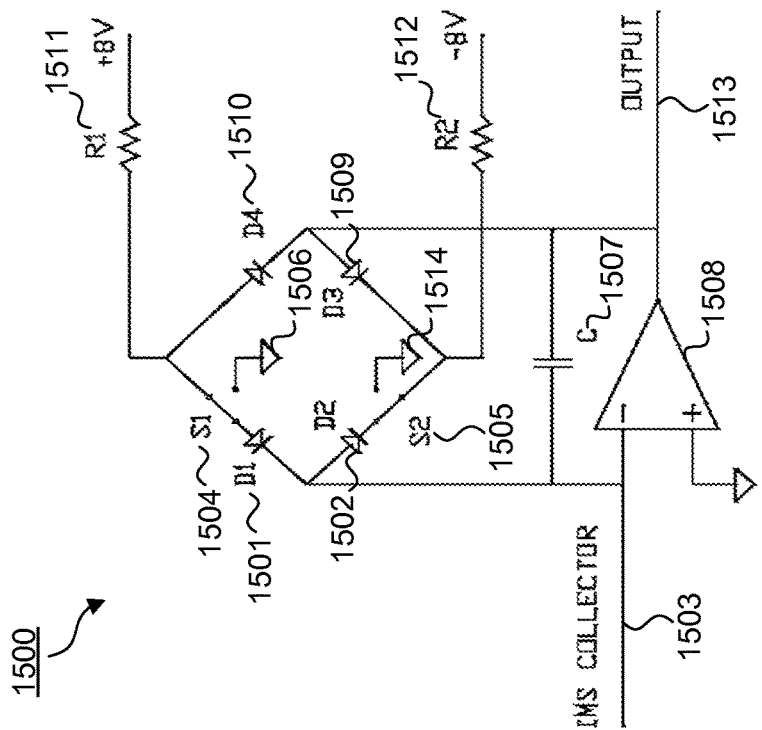
FIGS. 15 and 16 depict a further switch consistent with an embodiment of the circuit of FIG. 13.
Figure 15:
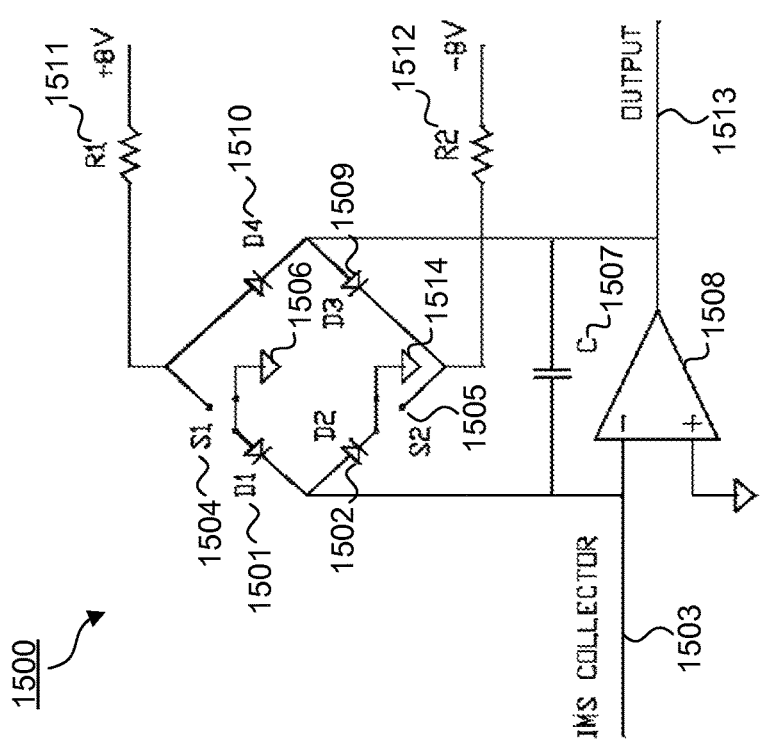

FIGS. 15 and 16 depict another embodiment of the preamplifier of FIG. 13 with a switch. FIG. 15 depicts a circuit 1500 which can be used in place of IC 1304 of FIG. 13. Two states of the circuit 1500 are shown; the 'SWITCH OPEN' state depicted in FIG. 15 and the 'SWITCH CLOSED' state depicted in FIG. 16. The 'SWITCH OPEN' state depicted in FIG. 15 corresponds to the open setting of switch 1303 and the 'SWITCH CLOSED' state depicted in FIG. 16 corresponds to the closed setting of switch 1303—and which is connected to the RESET operation discussed above.

A diode D1 1501 and a diode D2 1502 can be connected between an input node 1503 and two switches, S1 1504 and S2 1505. During operation in positive ion mode or negative ion mode, the diodes 1501 and 1502 can be switched to ground 1506 and 1514. The input node 1503 can be held at virtual ground by a feedback capacitor C 1507 across an amplifier 1508. The equivalent series resistance of the diodes 1501 and 1502 at 0 V bias can be very high; close to TΩs therefore, there can be virtually no current flowing through those diodes 1501 and 1502 even if there is small offset voltage (typically ~1 mV) present on the input node 1503.

During RESET, (i.e., during polarity switchover), both switches, S1 1504 and S2 1505 can be flipped, as illustrated in FIG. 16 thus connecting all four diodes 1501, 1502, 1509 and 1510 into a bridge configuration with all four diodes 1501, 1502, 1509 and 1510 forward biased. The bridge can act as a feedback resistor whose resistance equals to the equivalent series resistance of the diodes 1501, 1502, 1509 and 1510. The bias current used can be about 8 µA, the equivalent series resistance can be of the order of ~6 kΩ, which can be much less than the operating impedance of the circuit 1500 in the 'SWITCH OPEN' state as illustrated in FIG. 15. This keeps an output voltage 1513 close to 0 V even if input current reach 100 s of µA.

When the RESET signal terminates, the diodes D1 1501 and D2 1502 can be connected back to the ground 1506 and 1514, as depicted in FIG. 15. There can be a small charge on each diode 1501 and 1502 equal to forward voltage times diode capacitance. However, the two diodes 1501 and 1502 can have opposite charges, and when they are discharged, only the difference caused by mismatch of the charges becomes injected into the input 1503 of the circuit 1500. The total charge injected can be under 1 pA The amplifier 1508 can be, for example, a dual JFET (junction gate field-effect transistor), such as SST441 manufactured by Vishay Siliconix, driving a high precision low noise operational amplifier such as OPA2227 manufactured by Texas Instruments. Resistors R1 1511 and R2 1512 can be 1 MΩ each (i.e., they can be matched), diodes D3 1509 and D4 1510 can be a dual diode such as MMBD3004S manufactured by Diodes Incorporated, and the switches S1 1504 and S2 1505 can be implemented using a low capacitance, low charge injunction dual SPDT switch such as ADG1236 manufactured by Analog Devices.

Diodes D1 1501 and D2 1502 can be selected to have low capacitance and the largest possible equivalent series resistance. The design can use p-n junction JFET devices including, for example, SST-J212 manufactured by Vishal Siliconix.

Where data associated with a plasmagram is acquired during fast-switching clear-down mode, systems and methods consistent with yet another embodiment of the present disclosure can take into account a non-linearity that can be introduced into plasmagrams as a result of a fast-switching operation. Specifically, it is found that fast-switching can introduce a background distortion into the scan data that is processed to generate a plasmagram. An example of this distortion is illustrated in the plasmagram 1700 depicted in FIG. 17. Specially, the region 1701 and the region 1702 exhibit a baseline curve that is not even with the ordinate. A compensation for the non-linearity of this distortion can be accomplished by subtracting a value from a fitted curve from each value of the plasmagram in real-time before the plasmagram data (such as the segment data or the scan data) is analyzed by the processor 601 for clear-down characteristics. This can reduce the effect of the plasmagram non-linearity and allow the plasmagram background to approach the zero-level of the ordinate (i.e., it can normalize the measured values in time domain). Such an adjustment can assist in determining whether a clear-down characteristic (such as a residual signal associated with particular ions) is present in the segment data.

Figure 18:
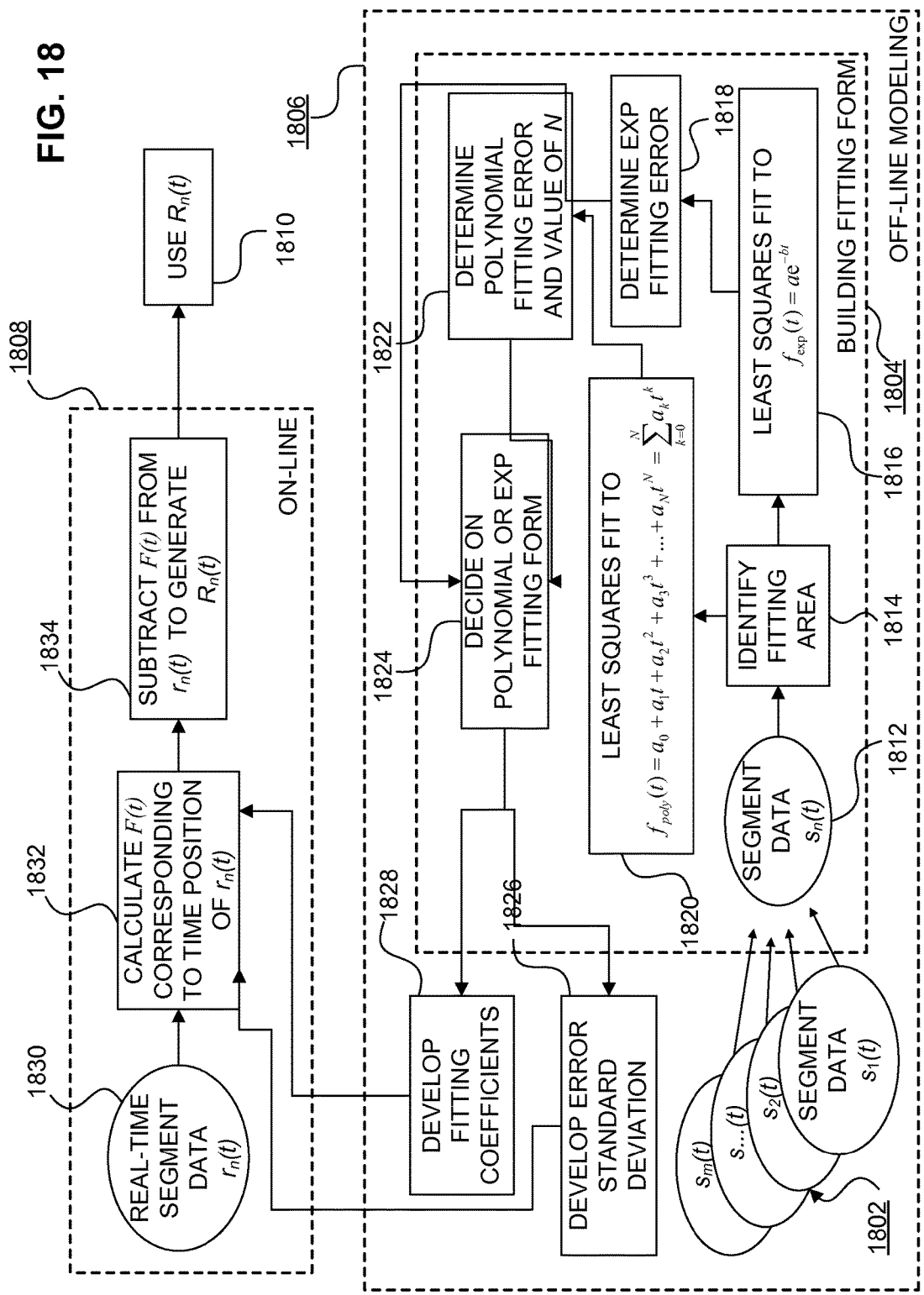
FIG. 18 schematically depicts steps associated with the normalization of the plasmagram of FIG. 17 consistent with an embodiment.

Steps associated with normalizing plasmagram data can generally be divided into two parts and is illustrated in FIG. 18. In the first part, an offline calculation 1806 can be performed on a collection 1802 of segment data associated with fast-polarity switching to develop, among other things, fitting coefficients (step 1828). In the second part 1808, these fitting coefficients can be used to subtract a portion of the amplitude from scan data values acquired by the collector 170 in real-time (i.e., as the scan data is collected, or prior to the analysis of the resulting segment data by the processor 601 for clear-down characteristics).

Figure 17:
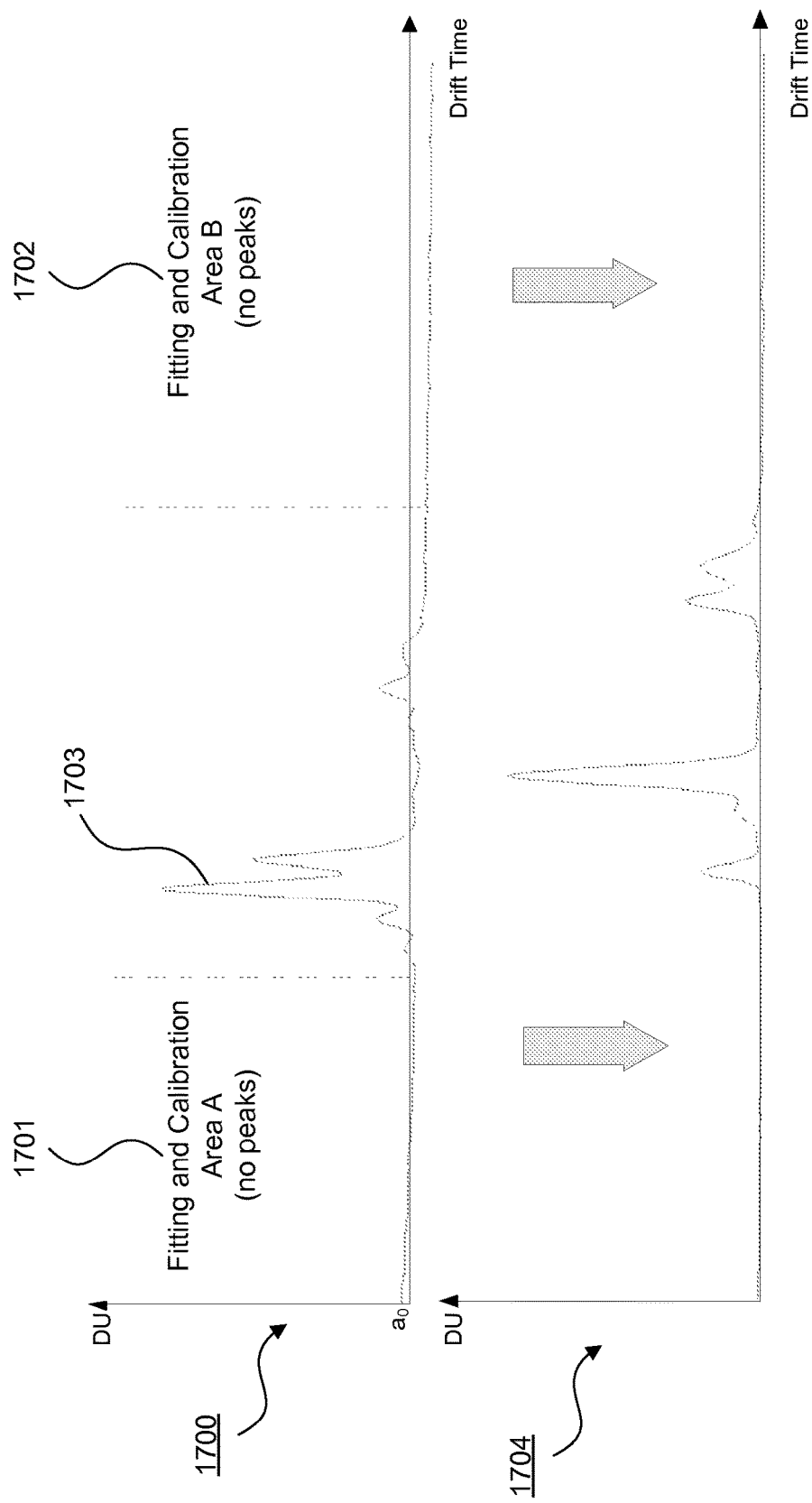
FIG. 17 depicts a plasmagram before and after it has been normalized.

The offline curve fitting calculation 1806 can include several steps. First, a sufficient number of clean plasmagrams (e.g., collections 1802 of segment data) can be collected such that a processor (which can be either processor 601, or another processor), under control of software instructions or otherwise, can perform a least-squares fitting of a fitting and calibration area of the plasmagram to a polynomial form (step 1820) or to an exponential form (step 1816). The regions of the plasmagram curves that are fitted—referred to as fitting and calibration areas—are illustrated in FIG. 17. Specifically, plasmagram 1700 includes Fitting and Calibration Area A (no peaks) 1701 and Fitting and Calibration Area B (no peaks) 1702. Fitting and Calibration Areas A 1701 and B 1702 can be selected or identified (step 1814) by the lack of significant peaks. Preferably, Fitting and Calibration Areas A 1201 and B 1202 can be selected to exhibit as little noise as possible. The segment data 1812 that can be used for the offline calculation 1806 can be collected—for example—from blank test samples, and when no chemicals have been introduced to the ion mobility spectrometer 100.

As indicated in FIG. 17, plasmagrams used for purposes of offline calculation 1806 can have relatively large fitting areas 1701 and 1702. The processor can perform a least squares fit of the selected fitting area to an exponential form $f_{exp}(t)=ae^{-bt}$ (step 1816) and define a fitting error (step 1818). The processor can also perform a least squares fit of the selected fitting area to polynomial form $$f_{poly}(t) = a_0 + a_1 t + a_2 t^2 + a_3 t^3 + \ldots + a_N t^N = \sum_{k=0}^{N} a_k t^k$$

(step 1820) and define a fitting error (step 1822). The region associated with the selected fitting areas can be fitted to either a polynomial or an exponential function, whichever gives better approximation (step 1824). (i.e., whichever approximation yields a smaller fitting error). The fitting error associated with step 1318 is the difference between the least squares fit to the exponential form $f_{exp}(t)=ae^{-bt}$ (step 1316) and the plasmagram data. The fitting error associated with step 1322 is the difference between the least squares fit to the polynomial form $$f_{poly}(t) = a_0 + a_1 t + a_2 t^2 + a_3 t^3 + \ldots + a_N t^N = \sum_{k=0}^{N} a_k t^k$$

(step 1320) and the plasmagram data.

Based upon which approximation yields a smaller fitting error (step 1824), the processor can determine whether to use the fitting to the exponential curve (step 1816) or the fitting to the polynomial curve (step 1820). This can be based on the value of fitting error, which can itself depend on the level of plasmagram noise. The processor can then identify a fitting form and average fitting coefficients (step 1828), which can be the result of many plasmagrams and instruments. The processor can also identify the standard deviation of fitting errors between collected plasmagrams (step 1826). The standard deviation can include the change in error associated with the same ion mobility spectrometer 100 and/or the change in error between different ion mobility spectrometers 100.

The calculation 1808 associated with the second part can be stored as software instructions in storage 602 and can be available to processor 601 as scan data and/or segment data is made available through collector interface 603. The processor 601 can be configured to collect all of the acquired data into a set $\{r_n(t)\}$ (step 1830). For each element $r_n(t)$ of the plasmagram set $\{r_n(t)\}$, the processor 601 can be configured to calculate the corresponding value of the fitted curve determined in step 1828 (F(t)) and any associated error (step 1826). It is possible to use a nested polynomial for faster calculation of F(t). The processor 601 can be configured to subtract this background contribution F(t) from each element of the plasmagram set $\{r_n(t)\}$ (step 1834). After such subtraction, the non-linear distortion, such as exhibited in the plasmagram 1700, can be eliminated. The end result can be plasmagram data (step 1810) with a flat baseline. Plasmagram 1704 in FIG. 17 depicts a curve similar to plasmagram 1700, but with the background distortion substantially eliminated.

Other embodiments of the invention will be apparent to those skilled in the art from consideration of the specification and practice of the embodiment disclosed herein. Although one or more methods have been described in conjunction with the ion mobility spectrometer 100 and/or the data processing system 600, it is to be apparent that the method may be used with other devices and configurations of ion mobility spectrometers. It is intended that the specification and examples be considered as exemplary only, with a true scope and spirit of the invention being indicated by the following claims.

We claim:

1. A method of clearing down an ion mobility spectrometer, the ion mobility spectrometer comprising an ionization region, and a drift region, the method comprising:
   receiving a clear-down trigger; and
   responsive to receipt of the clear-down trigger, fast-switching between a positive ion mode and a negative ion mode, wherein the fast-switching purges residual sample from the ionization region and/or the drift region of the ion mobility spectrometer, wherein, in the positive ion mode, an electric field is provided in a first direction from the ionization region along the drift region and in the negative ion mode the direction of the electric field is reversed, wherein no sample is added during the clear down, and wherein fast clearing-down comprises at least one of:
  operating in positive ion mode for less than one second before switching to operating in negative ion mode and operating in negative ion mode for less than one second, or
  operating in negative ion mode for less than one second before switching to operating in positive ion mode and operating in positive ion mode for less than one second.

2. The method of claim 1, wherein fast clearing-down comprises:
  operating in positive ion mode for between approximately 10 to 200 milliseconds before switching to operating in negative mode and operating in negative mode for between approximately 10 to 200 milliseconds; or
  operating in negative ion mode for between approximately 10 to 200 milliseconds before switching to operating in positive mode and operating in positive mode for between approximately 10 to 200 milliseconds.

3. The method of claim 1, wherein the residual sample comprises substances associated with at least a portion of the sample trapped in the ionization region prior to receipt of the clear-down trigger.

4. The method of claim 1, wherein the sample was introduced prior to receipt of the clear-down trigger.

5. The method of claim 1, wherein the clear-down trigger occurs:
  upon powering-down the ion mobility spectrometer;
  at a periodic interval; or
  upon determining that the residual sample is associated with a peak included in a plasmagram obtained before receipt of the clear-down trigger.

6. The method of claim 1, wherein the clear-down trigger occurs upon detection of ions associated with a predetermined substance by the ion mobility spectrometer.

7. The method of claim 1, wherein the clear-down trigger occurs upon detection of ions associated with at least one of a dopant, a calibrant, water, or oxygen during previous operation of the ion mobility spectrometer.

8. The method of claim 1, wherein fast clearing-down an ion mobility spectrometer comprises not receiving a sample during fast clearing-down.

9. The method of claim 1, further comprising terminating fast clearing-down the ion mobility spectrometer responsive to a determination that a residual signal is not present.

10. The method of claim 1, further comprising providing an option to implement fast clearing-down in response to the clear-down trigger.

11. The method of claim 1, wherein the ion mobility spectrometer further comprises a fixed grid and a gating grid, wherein in the positive ion mode the gating grid is at a higher voltage than the fixed grid, and wherein in the negative ion mode the gating grid is at a lower voltage than the fixed grid.

12. A method of clearing down an ion mobility spectrometer, the ion mobility spectrometer comprising an ionization region, and a drift region, the method comprising:
  receiving a clear-down trigger; and
  responsive to receipt of the clear-down trigger, fast-switching between a positive ion mode and a negative ion mode, wherein the fast-switching purges residual sample from the ionization region and/or the drift region of the ion mobility spectrometer, wherein, in the positive ion mode, an electric field is provided in a first direction from the ionization region along the drift region and in the negative ion mode the direction of the electric field is reversed, wherein no sample is added during the clear down, and wherein fast clearing-down comprises at least one of:
  operating in positive ion mode for 10 milliseconds to one minute before switching to operating in negative ion mode and operating in negative ion mode for 10 milliseconds to one minute, or
  operating in negative ion mode for 10 milliseconds to one minute before switching to operating in positive ion mode and operating in positive ion mode for 10 milliseconds to one minute.

13. The method of claim 12, wherein fast clearing-down comprises:
  operating in positive ion mode for between approximately 200 milliseconds to one minute before switching to operating in negative mode and operating in negative mode for between approximately 200 milliseconds to one minute, or
  operating in negative ion mode for between approximately 200 milliseconds to one minute before switching to operating in positive mode and operating in positive mode for between approximately 200 milliseconds to one minute.

14. A ion mobility spectrometer comprising: an ionization region including an ionization source that is configured to fast-clear down the ion mobility spectrometer, wherein no sample is added during the clear down, to purge residual sample that remains in the ionization region after receipt of a clear-down trigger by:
  operating in positive ion mode for less than one second before switching to operating in negative ion mode and operating in negative ion mode for less than one second, or
  operating in negative ion mode for less than one second before switching to operating in positive ion mode and operating in positive ion mode for less than one second.

15. The ion mobility spectrometer of claim 14, wherein the ion source is configured to purge residual sample that remains in the ionization region after receipt of a clear-down trigger by:
  operating in positive ion mode for 10 to 200 milliseconds before switching to operating in negative ion mode and operating in negative ion mode for 10 to 200 milliseconds, or
  operating in negative ion mode 10 to 200 milliseconds before switching to operating in positive ion mode and operating in positive ion mode for 10 to 200 milliseconds.

16. The ion mobility spectrometer of claim 14, wherein the clear-down trigger occurs upon detection of ions associated with a predetermined substance by the ion mobility spectrometer.

17. The ion mobility spectrometer of claim 14, wherein the residual sample is a portion of a sample that was introduced prior to receipt of the clear-down trigger.

18. The ion mobility spectrometer of claim 14, wherein the clear-down trigger occurs upon detection of ions from a sample associated with the residual sample.

19. The ion mobility spectrometer of claim 14, wherein the residual sample comprises ions that remain in the ionization region after detection of ions associated with at least a portion of a sample associated with the residual sample.

20. The ion mobility spectrometer of claim 14, wherein the ion mobility spectrometer is associated with a data processing system that is configured to output an option to clear-down the ion mobility spectrometer responsive to receipt of the clear-down trigger.

* * * * *